US008927726B2

(12) United States Patent
Himmelsbach et al.

(10) Patent No.: US 8,927,726 B2
(45) Date of Patent: Jan. 6, 2015

(54) N-CYCLOPROPYL-N-PIPERIDINYL-AMIDE DERIVATIVES, PHARMACEUTICAL COMPOSITIONS CONTAINING THEM AND USES THEREOF

(71) Applicants: Frank Himmelsbach, Mittelbiberach (DE); Elke Langkopf, Biberach an der Riss (DE); Neil J. Ashweek, Escondido, CA (US); Nicole Harriott, San Diego, CA (US)

(72) Inventors: Frank Himmelsbach, Mittelbiberach (DE); Elke Langkopf, Biberach an der Riss (DE); Neil J. Ashweek, Escondido, CA (US); Nicole Harriott, San Diego, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/947,200

(22) Filed: Jul. 22, 2013

(65) Prior Publication Data

US 2014/0031369 A1  Jan. 30, 2014

(30) Foreign Application Priority Data

Jul. 24, 2012 (EP) .................................... 12177724

(51) Int. Cl.
| | | |
|---|---|---|
| A61K 31/445 | (2006.01) | |
| C07D 401/00 | (2006.01) | |
| C07D 413/12 | (2006.01) | |
| A61K 31/454 | (2006.01) | |
| A61K 31/4545 | (2006.01) | |
| A61K 31/497 | (2006.01) | |
| A61K 31/506 | (2006.01) | |
| A61K 45/06 | (2006.01) | |
| C07D 401/12 | (2006.01) | |
| C07D 401/14 | (2006.01) | |

(52) U.S. Cl.
CPC ............ *C07D 413/12* (2013.01); *A61K 31/454* (2013.01); *A61K 31/4545* (2013.01); *A61K 31/497* (2013.01); *A61K 31/506* (2013.01); *A61K 45/06* (2013.01); *C07D 401/12* (2013.01); *C07D 401/14* (2013.01)
USPC .......................................... 546/208; 514/318

(58) Field of Classification Search
None
See application file for complete search history.

(56) References Cited

U.S. PATENT DOCUMENTS

2010/0331295 A1* 12/2010 Busch et al. ............. 514/210.18

FOREIGN PATENT DOCUMENTS

| WO | 2005061489 A1 | 7/2005 |
|---|---|---|
| WO | 2006070208 A1 | 7/2006 |
| WO | 2007145834 A2 | 12/2007 |
| WO | 2008025798 A1 | 3/2008 |
| WO | 2009117421 A2 | 9/2009 |

OTHER PUBLICATIONS

International Search Report and written opinion PCT/EP2013065160, mailed Sep. 24, 2013.
Database Registry, Chemical Abstracts Service, 2012, Database accession No. 1355632-12-0 abstract.
Database Registry, Chemical Abstracts Service, 2011, Database accession No. 1319926-76-5, abstract.
Database Registry, Chemical Abstracts Service, 2011, Database accession No. 1311739-36-2.
Database Registry, Chemical Abstracts Service, 2011, Database accession No. 1311445-65-4, abstract.
Database Registry, Chemical Abstracts Service, 2011, Databse accession No. 1280980-73-5, abstract.
Database Registry, Chemical Abstracts Service, 2011, Database accession No. 12580750-43-4.
Database Registry, Chemical Abstracts Service, 2010, Database accession No. 1252280-90-2, abstract.
Database Registry, Chemical Abstracts Service, 2010, Database accession No. 1252143-37-5, abstract.
Database Registry, Chemical Abstracts Service, 2012, Database accession No. 1390455-00-1, abstract.
Database Registry, Chemical Abstracts Service, 2013, Database accession No. 1436120-84-1, abstract.

* cited by examiner

*Primary Examiner* — Heidi Reese
(74) *Attorney, Agent, or Firm* — Michael P. Morris; Timothy X. Witkowski

(57) ABSTRACT

The present invention relates to compounds of general formula I, wherein $R^1$, $L^P$, $(Het)Ar^1$, $(Het)Ar^2$ and n are as defined in the application, which have valuable pharmacological properties, and in particular bind to the GPR119 receptor and modulate its activity.

11 Claims, No Drawings

N-CYCLOPROPYL-N-PIPERIDINYL-AMIDE DERIVATIVES, PHARMACEUTICAL COMPOSITIONS CONTAINING THEM AND USES THEREOF

This application claims priority to European Patent Application No. 12 177 724.7, filed Jul. 24, 2012, the contents of which are hereby incorporated by reference in its entirety.

FIELD OF THE INVENTION

The present invention relates to new compounds, in particular compounds of formula I

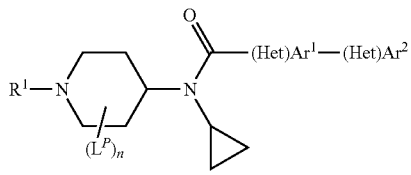

wherein $R^1$, $L^P$, $(Het)Ar^1$, $(Het)Ar^2$ and n are defined as hereinafter, to processes for preparing such compounds, to their use as modulators of the G-protein-coupled receptor GPR119, to methods for their therapeutic use, in particular to methods of treating diseases and conditions mediated by the modulation of the G-protein-coupled receptor GPR119, and to pharmaceutical compositions comprising them.

BACKGROUND OF THE INVENTION

Diabetes mellitus is a serious metabolic disease which affects more than 100 million people worldwide. In the USA there are more than 12 million diabetics with 600,000 new cases diagnosed every year. The prevalence of diabetes mellitus is increasing, which means in particular a high frequency of complications as well, leading to a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value ~0.9%). Moreover, glycaemic control deteriorated considerably over time even in patients in the intensive treatment group, and this was put down to a deterioration in beta cell function. Diabetes is also a major cause of damage to the retina at the back of the eye and increases the risk of cataract and glaucoma. Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the molecular mechanisms that are involved in obesity/diabetes syndromes are not yet clear. At an early stage of the development of obesity, an increased insulin secretion balances out the insulin resistance and protects the patient from hyperglycaemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown. Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

Dyslipidemia is a disorder of lipoprotein metabolism, including lipoprotein overproduction or deficiency. Dyslipidemias may be manifested by elevation of the total cholesterol, LDL cholesterol and triglyceride and free fatty acid concentrations, and a decrease in high-density lipoprotein (HDL) cholesterol concentration in the blood. Dyslipidemia occurs often in situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

GPR119 is a G-protein coupled receptor (also known as GPCR2, RUP3, SNORF25 or GDIR) which is expressed predominantly in the beta cells of the pancreas and in the K- and L-cells of the intestine. The GPR119 receptor and isoforms have been identified in mammalian species including human, rat, mouse, hamster, chimpanzee, rhesus monkey, cattle and dog. The expression of GPR119 in the pancreas and particularly in the pancreatic β-cells led to the hypothesis that the GPR119 receptor could have effects upon insulin secretion. Activation of the receptor stimulates the cAMP signal pathway, increasing the intracellular levels of cAMP in these cells. This will lead to an improved diabetic situation by a dual action of such a compound: stimulation of cAMP in the beta cell occurs directly via activation of GPR119 in these cells and furthermore indirectly via stimulation of the release of neuroendocrine peptides like GIP and GLP-1 and PYY from the gut. The release of these peptides may have also additional beneficial effects, e.g. on food intake, gastric emptying and other yet unknown functions. Also, a GPR119 agonist can be expected to bring about an improvement in the beta cell function and the beta cell mass. In fact, activation of GPR119 stimulates insulin secretion in-vitro and in-vivo (in rodents) in a glucose-dependent manner. The discovery of two endogenous ligands, lysophospha-tidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm. 2005, 744-751; Cell Metabolism 2006, 167-175; Endocrinolgy 2007, 2601-9). It has recently been shown that GPR119 agonists effectively lower the blood glucose levels in diabetic rodents without the risk of hypoglycaemia. GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Therefore the GPR119 agonists may be expected to have a therapeutic benefit in metabolic diseases. Examples of such diseases include type 1 diabetes, type 2 diabetes, insufficient glucose tolerance, insulin resistance, hyper-glycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis). For comparison and additional information also see 1. Dhayal, S., Morgan, N. G. The significance of GPR119 agonists as a future treatment for type 2 diabetes. Drug News Perspect. 2010, 23(7), 418-24.
2. Yoshida, S., Tanaka, H., Oshima, H., Yamazaki, T., Yonetoku, Y., Ohishi, T., Matsui, T., Shibasaki, M. AS1907417, a novel GPR119 agonist, as an insulinotropic and β-cell preservative agent for the treatment of type 2 diabetes. Biochem Biophys Res Commun. 2010, 400(4), 745-51.
3. Jones, R. M., Leonard, J. N., Buzard, D. J., Lehman, J. GPR119 agonists for the treatment of type 2 diabetes. Expert Opinion on Therapeutic Patents 2009, Vol. 19, No. 10: 1339-1359.

AIM OF THE PRESENT INVENTION

The aim of the present invention is to provide new compounds, in particular new N-cyclopropyl-N-piperidinyl-amide derivatives, which are active with regard to the G-protein-coupled receptor GPR119.

Another aim of the present invention is to provide new compounds, in particular new N-cyclopropyl-N-piperidinyl-amide derivatives, which are agonists of the G-protein-coupled receptor GPR119.

A further aim of the present invention is to provide new compounds, in particular new N-cyclopropyl-N-piperidinyl-amide derivatives, which have an activating effect on the G-protein-coupled receptor GPR119 in vitro and/or in vivo and possess suitable pharmacological and pharmacokinetic properties to use them as medicaments.

A further aim of the present invention is to provide effective GPR119 agonists, in particular for the treatment of metabolic disorders, for example diabetes, dyslipidemia and/or obesity.

A further aim of the present invention is to provide methods for treating a disease or condition mediated by the activation the G-protein-coupled receptor GPR119 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular N-cyclopropyl-N-piperidinyl-amide derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

It has now been found that the compounds according to the invention described in more detail hereinafter have surprising and particularly advantageous properties, in particular as GPR119 agonists.

In a first aspect the invention thus relates to compounds of formula I

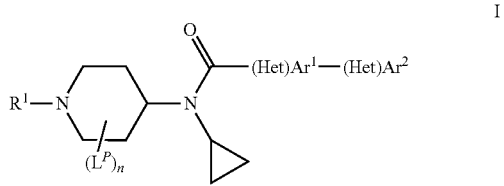

wherein
$R^1$ Is selected from the group $R^1$-G1 consisting of —$CH_2$—$R^a$, wherein $R^a$ denotes
  $C_{1-6}$-alkyl optionally mono- or polysubstituted with fluorine, or
  $C_{3-6}$-cycloalkyl optionally mono- or polysubstituted with fluorine and optionally substituted with a group selected from among $CH_3$, $CF_3$, and $CHF_2$;
$R^N$ is independently selected from the group $R^N$-G1 consisting of H, $C_{1-4}$-alkyl, $C_{1-4}$-alkyl-C(=O)— and $C_{1-4}$-alkyl-S(=O)$_2$—;
(Het)$Ar^1$ is selected from the group (Het)$Ar^1$-G1 consisting of phenyl and a 5- or 6-membered heteroaromatic ring which contains 1, 2 or 3 heteroatoms independently of each other selected from N, $NR^N$, O and S,
  wherein each phenyl and heteroaromatic ring is optionally substituted with one or more substituents selected from $L^Q$;
(Het)$Ar^2$ is selected from the group (Het)$Ar^2$-G1 consisting of:
  phenyl, tetrazolyl and a 5- or 6-membered heteroaromatic ring which contains 1, 2 or 3 heteroatoms independently of each other selected from N, $NR^N$, O and S,
  wherein each of said phenyl and heteroaromatic rings are optionally substituted with one or more substituents independently of each other selected from $L^{Ar}$, and
  wherein said phenyl, tetrazolyl and heteroaromatic ring are optionally monosubstituted with T;
  and 1,2,3,6-tetrahydropyridin-4-yl which is substituted at the N atom with a —S(=O)$_2$—($C_{1-6}$-alkyl) or —S(=O)$_2$—($C_{3-6}$-cycloalkyl) group,
  wherein the alkyl and cycloalkyl groups are optionally substituted with one or more substituents independently of each other selected from F, Cl, CN, OH and $C_{1-3}$-alkyl-O—;
T is selected from the group T-G1 consisting of F, Cl, Br, I, CN, OH, $NO_2$, $C_{1-6}$-alkyl, $C_{2-6}$-alkenyl, $C_{2-6}$-alkynyl, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C(=O)—, $C_{1-4}$-alkyl-S(=O)—, $C_{1-4}$-alkyl-S(=O)$_2$—, $R^{NT1}R^{NT2}N$—, $R^{NT1}R^{NT2}N$—C(=O)—, $R^{NT1}R^{NT2}N$—S (=O)$_2$—, R$^{NT1}$R$^{NT2}$N—C(=O)—(R$^N$)N—, heterocyclyl, heterocyclyl-O—, aryl, aryl-O—, heteroaryl and heteroaryl-O—,
  wherein each alkyl, alkenyl, alkynyl, and cycloalkyl group may be optionally substituted with one or more substituents independently of each other selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl and heterocyclyl, and
  wherein aryl denotes phenyl or naphthyl, and
  wherein heteroaryl is a 5- or 6-membered aromatic ring which contains 1, 2, 3 or 4 heteroatoms independently of each other selected from N, NR$^N$, O and S, and
  wherein heterocyclyl is a 4- to 7-membered unsaturated or saturated carbocyclic ring in which 1, 2, or 3 -CH$_2$-groups are replaced independently of each other by NR$^N$, O, —C(=O)—, S, —S(=O)— or —S(=O)$_2$—, and/or in which a —CH-group is replaced by N, and
  wherein each aryl, heteroaryl or heterocyclyl group may optionally be substituted with one or more substituents independently of each other selected from L$^{Ar}$;
R$^{NT1}$ is selected from the group R$^{NT1}$-G1 consisting of H, C$_{1-6}$-alkyl, C$_{3-6}$-cycloalkyl, C$_{1-6}$-alkyl-C(=O)—, C$_{1-6}$-alkyl-S(=O)$_2$—, heterocyclyl, aryl and heteroaryl,
  wherein each alkyl and cylcoalkyl group may be optionally substituted with one or more substituents independently of each other selected from the group consisting of F, OH, CN, C$_{1-4}$-alkyl, C$_{1-4}$-alkyl-O—, (R$^N$)$_2$N, C$_{1-4}$-alkyl-S(=O)$_2$—, C$_{3-6}$-cycloalkyl, heterocyclyl, phenyl and heteroaryl, and
  wherein heterocyclyl is a C$_{4-7}$-cycloalkyl ring in which 1 or 2 -CH$_2$— groups independently of each other are replaced by NR$^N$, O, C(=O), S, S(=O) or S(=O)$_2$, and
  wherein heterocyclyl may be optionally substituted with one or more substituents independently of each other selected from F, C$_{1-4}$-alkyl, (R$^N$)$_2$N, OH and C$_{1-4}$-alkyl-O—, and
  wherein aryl is phenyl or naphthyl, and
  wherein heteroaryl is a 5- or 6-membered aromatic ring which contains 1, 2 or 3 heteroatoms independently of each other selected from N, NR$^N$, O and S, and
  wherein each aryl, phenyl and heteroaryl is optionally substituted with one or more substituents L$^{Ar}$;
R$^{NT2}$ is selected from the group R$^{NT2}$-G1 consisting of H and C$_{1-6}$-alkyl; or
R$^{NT1}$ and R$^{NT2}$ are linked to form one group selected from the group R$^{NT1}$R$^{NT2}$-G1 consisting of C$_{3-5}$-alkylene,
  wherein 1 or 2 -CH$_2$-groups are replaced independently of each other by NR$^N$, O, C(=O), S, S(=O) or S(=O)$_2$, and
  wherein the ring formed by R$^{NT1}$ and R$^{NT2}$ together with the nitrogen atom to which they are attached is optionally substituted with one or more substituents independently of each other selected from F, C$_{1-4}$-alkyl, (R$^N$)$_2$N—, OH and C$_{1-4}$-alkyl-O—;
L$^{Ar}$ is selected from the group L$^{Ar}$-G1 consisting of F, Cl, Br, I, CN, OH, NO$_2$, C$_{1-4}$-alkyl-, C$_{1-4}$-alkyl-O—, (R$^N$)$_2$N—C(=O)—, (R$^N$)$_2$N— and C$_{1-4}$-alkyl-S(=O)$_2$—, wherein each alkyl group may be optionally substituted with one or more substituents independently of each other selected from F, Cl, CN, OH and C$_{1-3}$-alkyl-O—;
L$^P$ is selected from the group L$^P$-G1 consisting of F and C$_{1-3}$-alkyl, wherein the alkyl group may be substituted with one or more F-atoms;
L$^Q$ is selected from the group L$^Q$-G1 consisting of F, Cl, CN, OH, C$_{1-4}$-alkyl, C$_{3-7}$-cycloalkyl, F$_2$HC—, F$_3$C—, C$_{1-4}$-alkyl-O—, F$_2$HC—O—, F$_3$C—O— and C$_{3-7}$-cycloalkyl-O—; and
n is an integer selected from 0, 1, 2, 3, or 4;
including any tautomers and stereoisomers thereof,
or a salt thereof
or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR119 in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR119 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are mediated by the activation of the G-protein-coupled receptor GPR119.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly R$^1$, R$^N$, (Het)Ar$^1$, (Het)Ar$^2$, T, R$^{NT1}$, R$^{NT2}$, L$^{Ar}$, L$^P$, L$^Q$, and n are as defined above and hereinafter. If residues, substituents, or groups occur several times in a compound, as for example $R^N$, $L^{Ar}$, $L^P$, or $L^Q$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore and hereinafter.

$R^1$-G2:

According to one embodiment the group $R^1$ is selected from the group $R^1$-G2 consisting of:

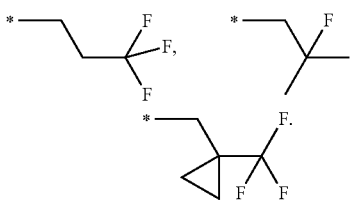

and $R^1$-G3:

In another embodiment the group $R^1$ is selected from the group $R^1$-G3 consisting of:

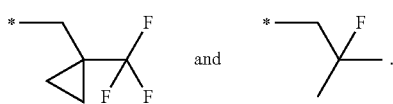

(Het)Ar$^1$:

(Het)Ar$^1$-G1:

In one embodiment the group (Het)Ar$^1$ is selected from the group (Het)Ar$^1$-G1 as defined hereinbefore and hereinafter.

(Het)Ar$^1$-G2:

In another embodiment the group (Het)Ar$^1$ is selected from the group (Het)Ar$^1$-G2 consisting of phenylene, pyridinylene, pyridazinylene, pyrimidinylene, pyrazinylene, furanylene, thiophenylene, imidazolylene, pyrazolylene, oxazolylene, isoxazloylene, thiazolylene, triazolylene, oxadiazolylene and thiadiazolylene, wherein each group is optionally additionally substituted with one or two substituents independently of each other selected from $L^Q$.

(Het)Ar$^1$-G3:

In another embodiment the group (Het)Ar$^1$ is selected from the group (Het)Ar$^1$-G3 consisting of:

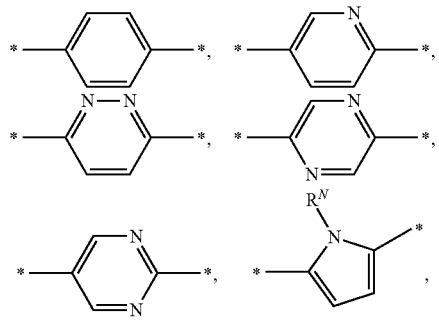

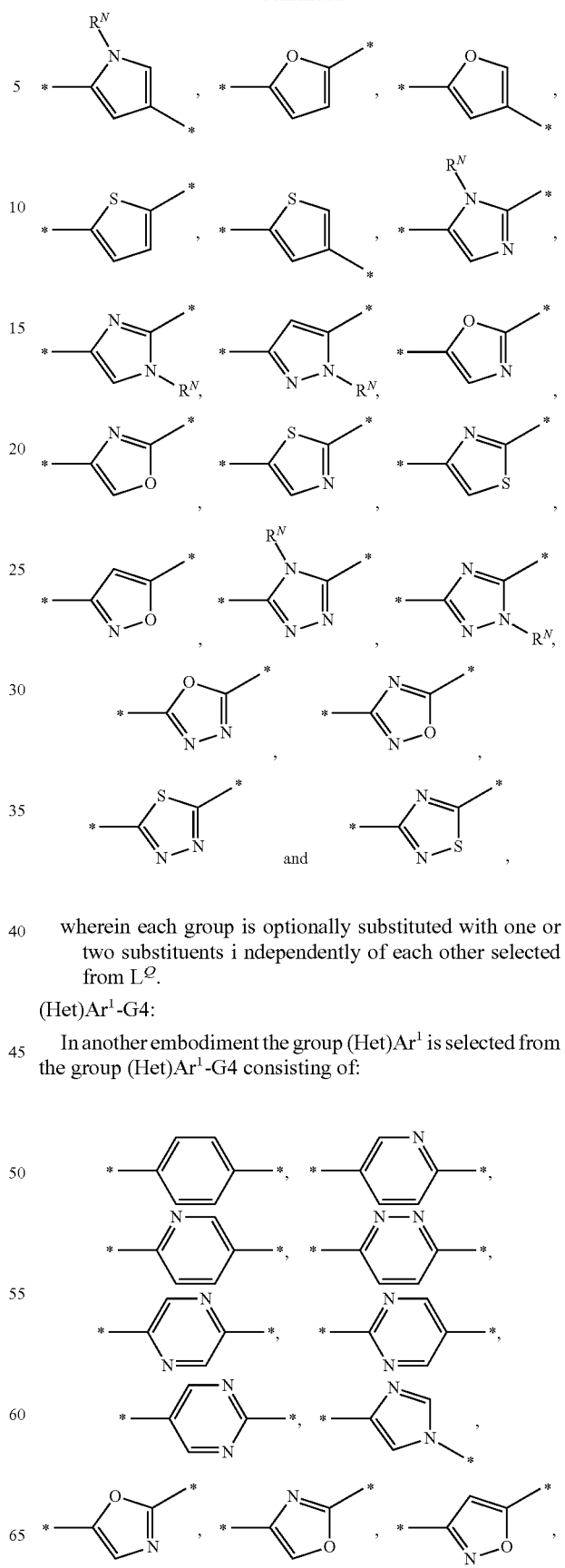

wherein each group is optionally substituted with one or two substituents independently of each other selected from $L^Q$.

(Het)Ar$^1$-G4:

In another embodiment the group (Het)Ar$^1$ is selected from the group (Het)Ar$^1$-G4 consisting of:

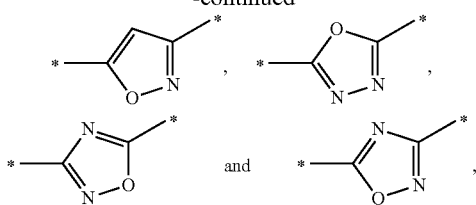 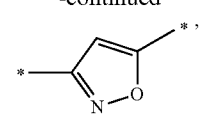

wherein the group (Het)Ar$^2$ is attached to the right-hand side and the carbonyl group figuring in formula I is attached to the left-hand side of each of the above-mentioned groups, and wherein each group is optionally substituted with one substituent selected from L$^Q$.

(Het)Ar$^1$-G5:

In another embodiment the group (Het)Ar$^1$ is selected from the group (Het)Ar$^1$-G5 consisting of

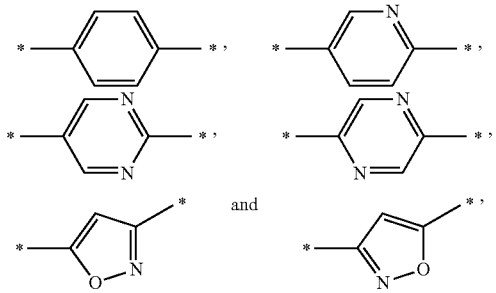

wherein the group (Het)Ar$^2$ is attached to the right-hand side and the carbonyl group figuring in formula I is attached to the left-hand side of each of the above-mentioned groups, and wherein the phenylene group is optionally additionally substituted with F.

(Het)Ar$^1$-G5a:

In another embodiment the group (Het)Ar$^1$ is selected from the group (Het)Ar$^1$-G5a consisting of

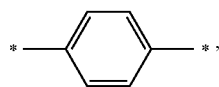

which is optionally additonally substituted with F.

(Het)Ar$^1$-G5b:

In another embodiment the group (Het)Ar$^1$ is selected from the group (Het)Ar$^1$-G5b consisting of:

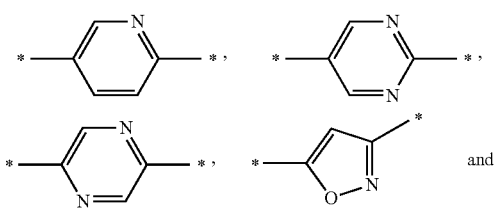

wherein the group (Het)Ar$^2$ is attached to the right-hand side and the carbonyl group figuring in formula I is attached to the left-hand side of each of the above-mentioned groups.

R$^N$

R$^N$-G1:

In one embodiment, the group R$^N$ is selected from the group R$^N$-G1 as defined hereinbefore and hereinafter.

R$^N$-G2:

In another embodiment the group R$^N$ is selected from the group R$^N$-G2 consisting of H, methyl, ethyl, isopropyl, methylcarbonyl, and methylsulfonyl.

R$^N$-G3:

In another embodiment the group R$^N$ is selected from the group R$^N$-G3 consisting of H, methyl, methylcarbonyl, and methylsulfonyl.

R$^N$-G4:

In another embodiment the group R$^N$ is selected from the group R$^N$-G4 consisting of H and methyl.

R$^N$-G5:

In another embodiment the group R$^N$ is selected from the group R$^N$-G5 consisting of H.

(Het)Ar$^2$:

(Het)Ar$^2$-G1:

In one embodiment, the group (Het)Ar$^2$ is selected from the group (Het)Ar$^2$-G1 as defined hereinbefore and hereinafter.

(Het)Ar$^2$-G2:

In another embodiment the group (Het)Ar$^2$ is selected from the group (Het)Ar$^2$-G2 consisting of phenyl, tetrazolyl, a 6-membered heteroaromatic ring which contains 1 or 2 N atoms, and a 5-membered heteroaromatic ring which contains 1, 2 or 3 heteroatoms independently of each other selected from N, NR$^N$, O and S;

wherein said phenyl, tetrazolyl, and heteroaromatic ring are optionally monosubstituted with T, and wherein said phenyl and heteroaromatic ring are optionally substituted with one or more substituents independently of each other selected from L$^{Ar}$;

and 1,2,3,6-tetrahydropyridin-4-yl which is substituted at the N atom with a —S(=O)$_2$—(C$_{1-6}$-alkyl) group, wherein the alkyl group is optionally substituted with 1 or 2 substituents independently of each other selected from F, Cl, CN, OH and H$_3$C—O—.

(Het)Ar$^2$-G3:

In another embodiment the group (Het)Ar$^2$ is selected from the group (Het)Ar$^2$-G3 consisting of phenyl, tetrazolyl, and a heteroaromatic ring selected from pyridinyl, pyrazinyl, pyridazinyl, pyrimidinyl, isoxazolyl, oxazolyl, oxadiazolyl, imidazolyl, pyrazolyl, triazolyl, thienyl and thiazolyl, wherein the above-mentioned groups are optionally monosubstituted with T, and wherein said phenyl and heteroaromatic ring are optionally substituted with one or more substituents independently of each other selected from L$^{Ar}$, and wherein in heteroaromatic ring the H-atom in one NH group is optionally replaced by R$^N$.

(Het)Ar$^2$-G4:

In another embodiment the group (Het)Ar$^2$ is selected from the group (Het)Ar$^2$-G4 consisting of phenyl, pyridyl, oxazolyl, imidazolyl, [1,2,4]triazolyl and tetrazolyl, wherein each of the beforementioned groups is optionally substituted with one or two substituents independently of each other selected from the group consisting of F, CN, CH$_2$CN, CH$_3$, CH$_2$CH$_3$, OCH$_2$CH$_3$ and SO$_2$CH$_3$.

(Het)Ar$^2$-G5:

In another embodiment the group (Het)Ar$^2$ is selected from the group (Het)Ar$^2$-G5 consisting of:

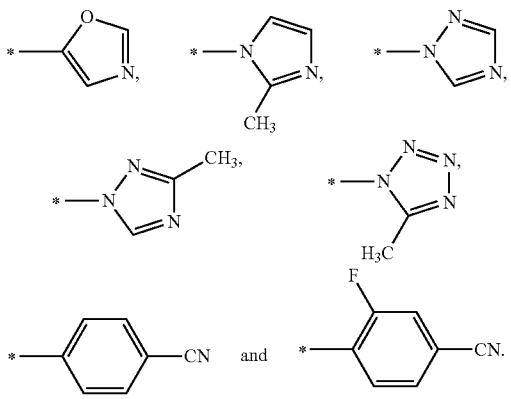

T

T-G1:

According to one embodiment, the group T is selected from the group T-G1 as defined hereinbefore and hereinafter.

T-G2:

According to another embodiment the group T is selected from the group T-G2 consisting of F, Cl, Br, CN, OH, C$_{1-4}$-alkyl, C$_{1-4}$-alkyl-O—, C$_{1-4}$-alkyl-O—C(=O)—, C$_{1-4}$-alkyl-C(=O)—, C$_{1-4}$-alkyl-S(=O)—, C$_{1-4}$-alkyl-S(=O)$_2$—, R$^{NT1}$R$^{NT2}$N—C(=O)—, R$^{NT1}$R$^{NT2}$N—S(=O)$_2$— and R$^{NT1}$R$^{NT2}$N, wherein each alkyl group may be optionally substituted with one or more substituents independently of each other selected from F, Cl, CN, OH, phenyl, heteroaryl and heterocyclyl, wherein heteroaryl is selected from the group consisting of pyridinyl, pyrimidinyl, pyridazinyl, pyrazinyl, pyrazolyl, imidazolyl, [1,2,4]triazolyl and tetrazolyl, and wherein heterocyclyl is selected from the group consisting of azetidinyl, pyrrolidinyl, piperidinyl, piperazinyl and morpholinyl, wherein in each of the beforementioned groups a —CH$_2$-group may be replaced by a group selected from —C(=O)— and —S(=O)$_2$—, and wherein each of the beforementioned groups may be optionally substituted with one or more substituents independently of each other selected from C$_{1-3}$-alkyl, and wherein phenyl and heteroaryl may be optionally substituted with one or more substituents L$^{Ar}$ which may be the same or different, and in addition the group T-G2 consists of R$^{NT1}$R$^{NT2}$N—C(=O)—C$_{1-4}$-alkyl- and C$_{1-4}$-alkyl-S(=O)$_2$—C$_{1-4}$-alkyl-.

T-G3:

According to another embodiment the group T is selected from the group T-G3 consisting of CN, C$_{1-3}$-alkyl, NC—C$_{1-3}$-alkyl-, C$_{1-3}$-alkyl-O—, C$_{1-3}$-alkyl-S(=O)—, C$_{1-3}$-alkyl-S(=O)$_2$—, R$^{NT1}$R$^{NT2}$N—S(=O)$_2$—, R$^{NT1}$R$^{NT2}$N—C(=O)—, R$^{NT1}$R$^{NT2}$N—, C$_{1-3}$-alkyl-S(=O)$_2$—CH$_2$— and R$^{NT1}$R$^{NT2}$N—C(=O)—CH$_2$—.

T-G4:

According to another embodiment the group T is selected from the group T-G4 consisting of CN, C$_{1-3}$-alkyl, NC—C$_{1-3}$-alkyl-, C$_{1-3}$-alkyl-O— and C$_{1-3}$-alkyl-S(=O)$_2$—.

T-G5:

According to another embodiment the group T is selected from the group T-G5 consisting of CN and —CH$_3$.

R$^{NT1}$

R$^{NT1}$-G1:

In one embodiment, R$^{NT1}$ is selected from the group R$^{NT1}$-G1 as defined hereinbefore and hereinafter.

R$^{NT1}$-G2:

In another embodiment R$^{NT1}$ is selected from the group R$^{NT1}$-G2 consisting of H, C$_{1-3}$-alkyl, C$_{3-6}$-cycloalkyl, C$_{1-4}$-alkyl-C(=O)— and C$_{1-4}$-alkyl-S(=O)$_2$—, wherein each alkyl and cylcoalkyl group is optionally substituted with one or more substituents independently of each other selected from the group consisting of F, OH, C$_{1-3}$-alkyl-O— and (R$^N$)$_2$N—.

R$^{NT1}$-G3:

In another embodiment R$^{NT1}$ is selected from the group R$^{NT1}$-G3 consisting of H, C$_{1-3}$-alkyl, C$_{1-3}$-alkyl-C(=O)— and C$_{1-3}$-alkyl-S(=O)$_2$—.

R$^{NT2}$

R$^{NT2}$-G1:

In one embodiment, R$^{NT2}$ is selected from the group R$^{NT2}$-G1 as defined hereinbefore and hereinafter.

R$^{NT2}$-G2:

In another embodiment R$^{NT2}$ is selected from the group R$^{NT2}$-G2 consisting of H and C$_{1-3}$-alkyl.

R$^{NT2}$-G3:

In another embodiment R$^{NT2}$ is selected from the group R$^{NT2}$-G3 consisting of H and CH$_3$.

R$^{NT2}$-G4:

In another embodiment R$^{NT2}$ is selected from the group R$^{NT2}$-G4 consisting of H.

R$^{NT1}$R$^{NT2}$

R$^{NT1}$R$^{NT2}$-G1:

According to another embodiment the groups R$^{NT1}$ and R$^{NT2}$ are linked and form a group which is selected from the group R$^{NT1}$R$^{NT2}$-G1 as defined hereinbefore and hereinafter.

R$^{NT1}$R$^{NT2}$-G2:

According to another embodiment the groups R$^{NT1}$ and R$^{NT2}$ are linked and together with the N-atom to which they are attached form a group which is selected from the group R$^{NT1}$R$^{NT2}$-G2 consisting of azetidinyl, pyrrolidinyl, piperidinyl, morpholinyl, piperazinyl, piperazin-2-onyl, N—(C$_{1-3}$-alkyl)-piperazinyl, N—(C$_{1-3}$-alkyl)-piperazin-2-onyl and N—(C$_{1-3}$-alkyl-C(=O))-piperazinyl, which are optionally substituted with one or more substituents independently of each other selected from the group consisting of F, OH, C$_{1-3}$-alkyl, C$_{1-3}$-alkyl-O— and (R$^N$)$_2$N—.

L$^{Ar}$:

L$^{Ar}$-G1:

In one embodiment, the group L$^{Ar}$ is selected from the group L$^{Ar}$-G1 as defined hereinbefore and hereinafter.

L$^{Ar}$-G2:

In another embodiment the group L$^{Ar}$ is selected from the group L$^{Ar}$-G2 consisting of F, Cl, Br, I, CN, OH, C$_{1-3}$-alkyl, C$_{1-3}$-alkyl-O—, H$_2$N—, C$_{1-3}$-alkyl-NH— and (C$_{1-3}$-alkyl)$_2$N—, wherein the C$_{1-3}$-alkyl and C$_{1-3}$-alkyl-O— group may be optionally substituted with one or more F-atoms.

L$^{Ar}$-G3:

In another embodiment the group L$^{Ar}$ is selected from the group L$^{Ar}$-G3 consisting of F, CN, OH, H$_3$C—, F$_3$C—, HF$_2$C—, H$_3$C—O—, HF$_2$C—O— and F$_3$C—O—.

$L^{Ar}$-G4:

According to the embodiment $L^{Ar}$-G4, the group $L^{Ar}$ is F.

$L^P$:

$L^P$-G1:

In one embodiment, the group $L^P$ is selected from the group $L^P$-G1 as defined hereinbefore and hereinafter.

$L^P$-G2:

In another embodiment the group $L^P$ is selected from the group $L^P$-G2 consisting of F and methyl.

$L^P$-G3:

According to the embodiment $L^P$-G3, the group $L^P$ is F.

$L^Q$:

$L^Q$-G1:

In one embodiment, the group $L^Q$ is selected from the group $L^Q$-G1 as defined hereinbefore and hereinafter.

$L^Q$-G2:

In another embodiment the group $L^Q$ is selected from the group $L^Q$-G2 consisting of F, CN, OH, $H_3C$—, $F_2HC$—, $F_3C$—, $H_3C$—O—, $F_2HC$—O— and $F_3C$—O—.

$L^Q$-G3:

In another embodiment the group $L^Q$ is selected from the group $L^Q$-G3 consisting of F and $H_3C$—.

$L^Q$-G4:

According to the embodiment $L^Q$-G4, the group $L^Q$ is F.

n:

The index n is an integer selected from 0, 1, 2, 3 or 4.

According to another embodiment the index n is 0, 1 or 2.

According to another embodiment the index n is 0 or 1.

According to another embodiment the index n is 1.

According to another embodiment the index n is 0.

The following preferred embodiments of compounds of the formula I are described using generic formulae 1.1 to 1.5, wherein any tautomers and stereoisomers, solvates, hydrates and salts thereof, in particular the pharmaceutically acceptable salts thereof, are encompassed.

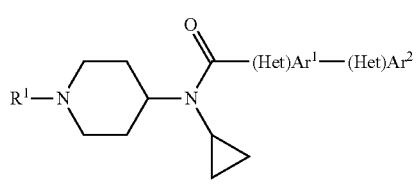

I.1

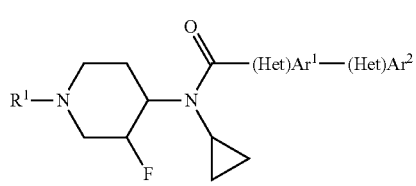

I.2

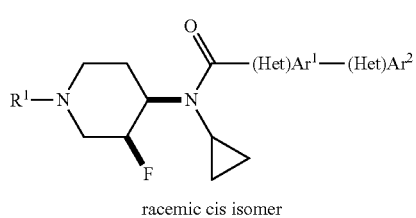

I.3 racemic cis isomer

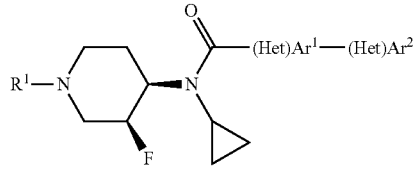

I.4

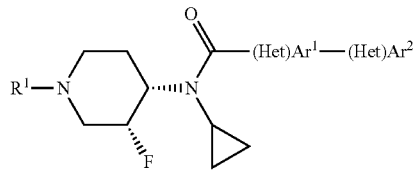

I.5 wherein the groups $R^1$, $(Het)Ar^1$, and $(Het)Ar^2$ are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | $R^1$ | $(Het)Ar^2$ | $(Het)Ar^1$ | $L^P$ | n |
|---|---|---|---|---|---|
| E-1 | $R^1$-G1 | $(Het)Ar^2$-G1 | $(Het)Ar^1$-G1 | $L^P$-G2 | 1 or 0 |
| E-2 | $R^1$-G2 | $(Het)Ar^2$-G1 | $(Het)Ar^1$-G1 | $L^P$-G2 | 1 or 0 |
| E-3 | $R^1$-G3 | $(Het)Ar^2$-G2 | $(Het)Ar^1$-G1 | $L^P$-G2 | 1 or 0 |
| E-4 | $R^1$-G3 | $(Het)Ar^2$-G1 | $(Het)Ar^1$-G2 | $L^P$-G2 | 1 or 0 |
| E-5 | $R^1$-G3 | $(Het)Ar^2$-G4 | $(Het)Ar^1$-G2 | $L^P$-G2 | 1 or 0 |
| E-6 | $R^1$-G3 | $(Het)Ar^2$-G2 | $(Het)Ar^1$-G4 | $L^P$-G2 | 1 or 0 |
| E-7 | $R^1$-G3 | $(Het)Ar^2$-G2 | $(Het)Ar^1$-G2 | $L^P$-G2 | 1 or 0 |
| E-8 | $R^1$-G3 | $(Het)Ar^2$-G2 | $(Het)Ar^1$-G2 | $L^P$-G3 | 1 or 0 |
| E-9 | $R^1$-G3 | $(Het)Ar^2$-G3 | $(Het)Ar^1$-G2 | $L^P$-G3 | 1 or 0 |
| E-10 | $R^1$-G3 | $(Het)Ar^2$-G2 | $(Het)Ar^1$-G3 | $L^P$-G3 | 1 or 0 |
| E-11 | $R^1$-G3 | $(Het)Ar^2$-G3 | $(Het)Ar^1$-G3 | $L^P$-G2 | 1 or 0 |
| E-12 | $R^1$-G3 | $(Het)Ar^2$-G4 | $(Het)Ar^1$-G4 | $L^P$-G2 | 1 or 0 |
| E-13 | $R^1$-G3 | $(Het)Ar^2$-G3 | $(Het)Ar^1$-G3 | $L^P$-G3 | 1 or 0 |
| E-14 | $R^1$-G3 | $(Het)Ar^2$-G4 | $(Het)Ar^1$-G3 | $L^P$-G3 | 1 or 0 |
| E-15 | $R^1$-G3 | $(Het)Ar^2$-G3 | $(Het)Ar^1$-G4 | $L^P$-G3 | 1 or 0 |
| E-16 | $R^1$-G3 | $(Het)Ar^2$-G4 | $(Het)Ar^1$-G4 | $L^P$-G3 | 1 or 0 |
| E-17 | $R^1$-G3 | $(Het)Ar^2$-G4 | $(Het)Ar^1$-G5 | $L^P$-G3 | 1 or 0 |
| E-18 | $R^1$-G2 | $(Het)Ar^2$-G5 | $(Het)Ar^1$-G5 | $L^P$-G3 | 1 or 0 |
| E-19 | $R^1$-G2 | $(Het)Ar^2$-G5 | $(Het)Ar^1$-G5a | $L^P$-G3 | 1 or 0 |
| E-20 | $R^1$-G2 | $(Het)Ar^2$-G5 | $(Het)Ar^1$-G5b | $L^P$-G3 | 1 or 0 |
| E-21 | $R^1$-G3 | $(Het)Ar^2$-G5 | $(Het)Ar^1$-G5 | $L^P$-G3 | 1 or 0 |
| E-22 | $R^1$-G3 | $(Het)Ar^2$-G5 | $(Het)Ar^1$-G5a | $L^P$-G3 | 1 or 0 |
| E-23 | $R^1$-G3 | $(Het)Ar^2$-G5 | $(Het)Ar^1$-G5b | $L^P$-G3 | 1 or 0 |

Another embodiment concerns those compounds of formula I, wherein $R^1$ is selected from a group consisting of

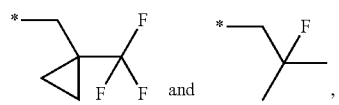

and $HetAr^1$-$(Het)Ar^2$ is selected from a group consisting of

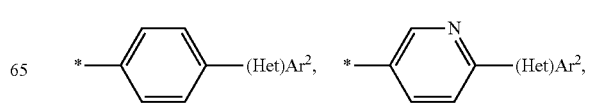

-continued

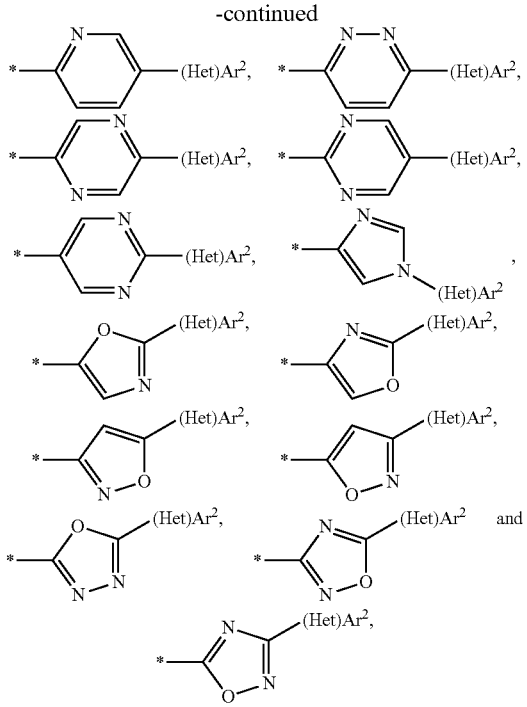

wherein the phenylene group is optionally additionally substituted with one F atom, and
wherein (Het)Ar² is selected from a group consisting of phenyl, pyridyl, oxazolyl, imidazolyl, [1,2,4]triazolyl and tetrazolyl,
  wherein each of them is optionally substituted with one or two substituents independently of each other selected from the group consisting of F, CN, —CH₂CN, —CH₃, —CH₂CH₃, —OCH₂CH₃ and —SO₂CH₃;
$L^P$ is F and n is 0 or 1.

Another embodiment concerns those compounds of formula I, wherein
R¹ is selected from a group consisting of

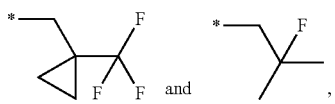

HetAr¹-(Het)Ar² is selected from a group consisting of

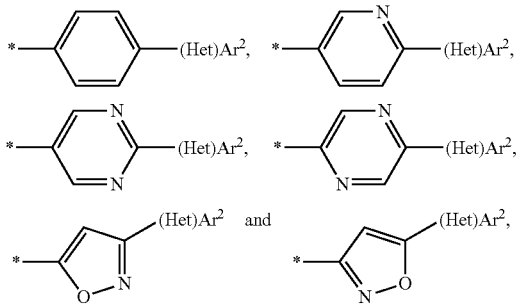

wherein the phenylene group is optionally additionally substituted with one F, and
wherein (Het)Ar² is selected from a group consisting of:

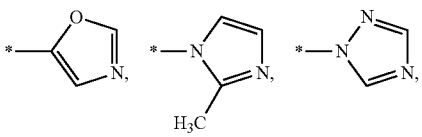

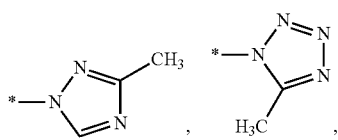

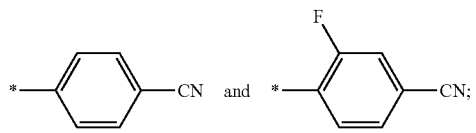

$L^P$ is F and n is 0 or 1.

Particularly preferred compounds, including their tautomers and stereoisomers, the salts thereof, or any solvates or hydrates thereof, are described in the experimental section hereinafter.

The following compounds are mentioned as preferred examples of compounds according to the invention:

| Example | Structure |
|---|---|
| 1 | 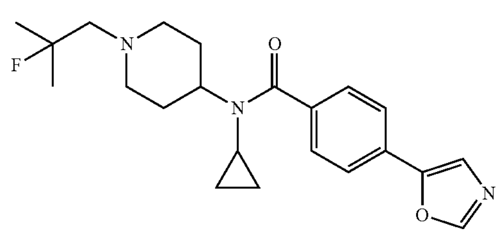 [SMILES: CC(C)(F)CN1CCC(N(C(=O)c2ccc(-c3cnco3)cc2)C2CC2)CC1] |

-continued
| Example | Structure |
|---|---|
| 2 | 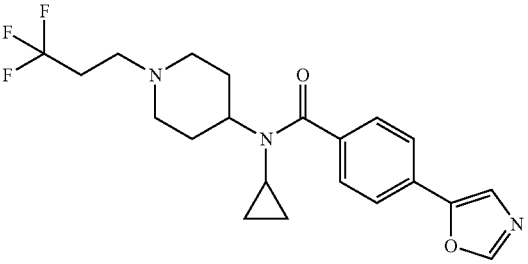 [SMILES: O=C(c1ccc(-c2cnco2)cc1)N(C1CC1)C1CCN(CCC(F)(F)F)CC1] |
| 3 | 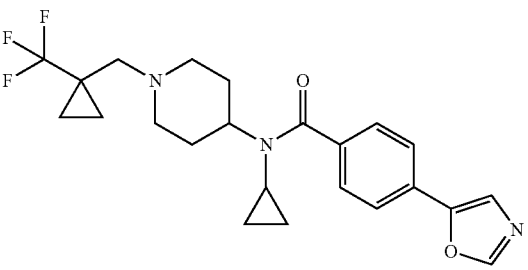 [SMILES: O=C(c1ccc(-c2cnco2)cc1)N(C1CC1)C1CCN(CC2(C(F)(F)F)CC2)CC1] |
| 4 | 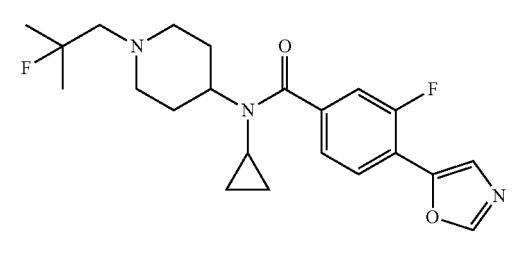 [SMILES: CC(C)(F)CN1CCC(N(C(=O)c2ccc(-c3cnco3)c(F)c2)C2CC2)CC1] |
| 5 | 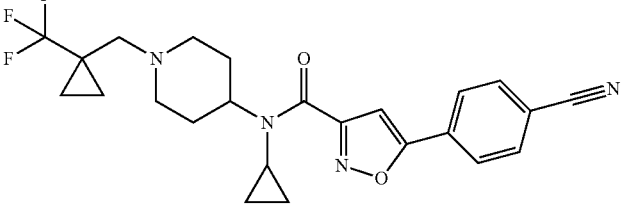 |
| 6 | 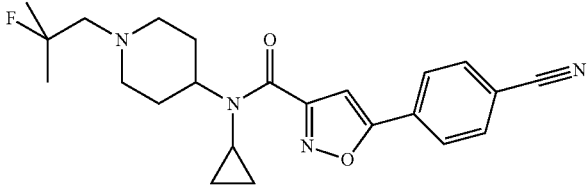 [SMILES: CC(C)(F)CN1CCC(N(C(=O)c2cc(-c3ccc(C#N)cc3)on2)C2CC2)CC1] |
| 7 | 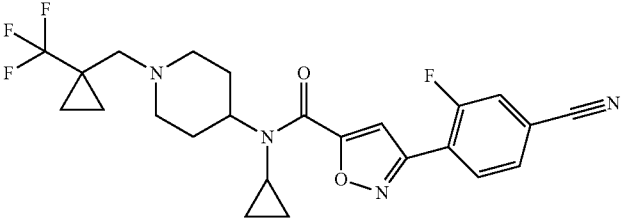 [SMILES: N#Cc1ccc(-c2cc(C(=O)N(C3CC3)C3CCN(CC4(C(F)(F)F)CC4)CC3)on2)c(F)c1] |

-continued
| Example | Structure |
|---------|-----------|
| 8 | 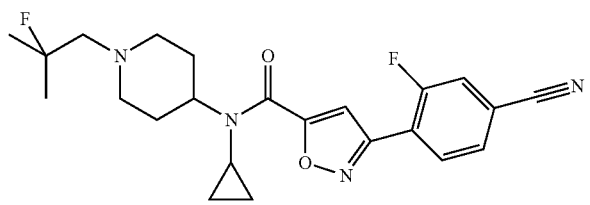 [SMILES: CC(C)(F)CN1CCC(N(C(=O)c2cc(-c3ccc(C#N)cc3F)no2)C2CC2)CC1] |
| 9 | 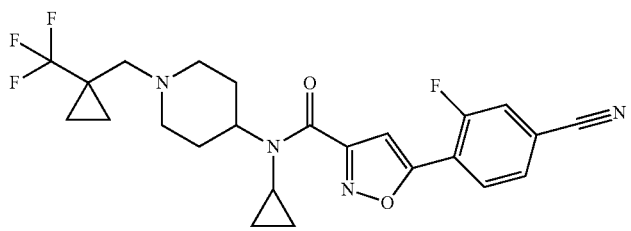 [SMILES: N#Cc1ccc(-c2cc(C(=O)N(C3CC3)C3CCN(CC4(C(F)(F)F)CC4)CC3)no2)c(F)c1] |
| 10 | 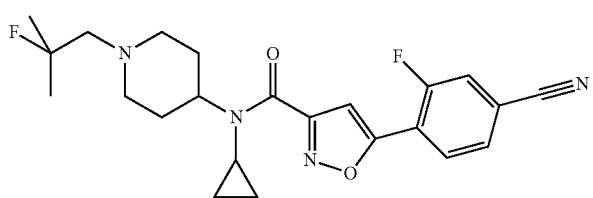 [SMILES: CC(C)(F)CN1CCC(N(C(=O)c2cc(-c3ccc(C#N)cc3F)on2)C2CC2)CC1] |
| 11 | 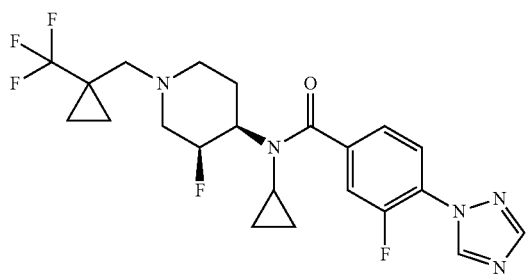 [SMILES: O=C(c1ccc(-n2cncn2)c(F)c1)N(C1CC1)[C@@H]1CCN(CC2(C(F)(F)F)CC2)C[C@@H]1F] |
| 12 | 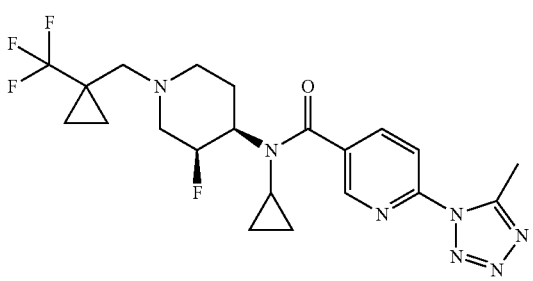 [SMILES: Cc1nnnn1-c1ccc(C(=O)N(C2CC2)[C@@H]2CCN(CC3(C(F)(F)F)CC3)C[C@@H]2F)cn1] |
| 13 | 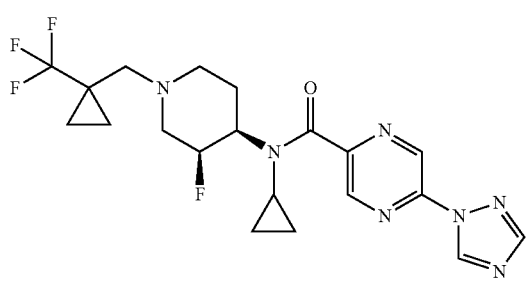 [SMILES: O=C(c1cnc(-n2cncn2)cn1)N(C1CC1)[C@@H]1CCN(CC2(C(F)(F)F)CC2)C[C@@H]1F] |

| Example | Structure |
|---------|-----------|
| 14 | ![Structure 14] |
| 15 | ![Structure 15] | including any tautomers and stereoisomers thereof, or a salt thereof or a solvate or hydrate thereof.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to one skilled in the art but are not described in detail here may also be used. The general processes for preparing the compounds according to the invention will become apparent to one skilled in the art on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to one skilled in the art.

The compounds of the invention I can principally be assembled from the building blocks 1 to 5 as sketched in Scheme 1; $R^1$, $L^P$, n, and Ar have the meanings as defined hereinbefore and hereinafter. Building blocks 1 to 5 are either known compounds that are commercially available or of which a synthesis is reported or can be synthesized in analogy to proceedings described herein or in the literature for related compounds. The order of linking the building blocks is variable and the most effective way depends on the precise structure of the building blocks and the reactivity of the groups to be linked and may vary for each of them. In principle, almost every order of linking is conceivable, however, combining building block 1 with building block 2 followed by attachment of building block 3 and finally compound 4, optionally already bearing building block 5, is preferred in most of the cases. For varying one individual residue or for the synthesis of particular target compounds a deviating proceeding may be more appropriate.

Scheme 1

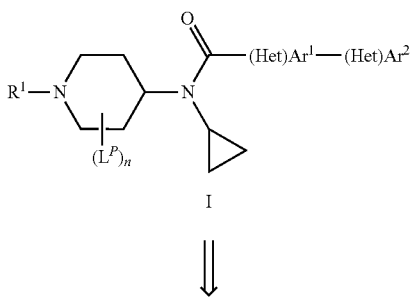

I

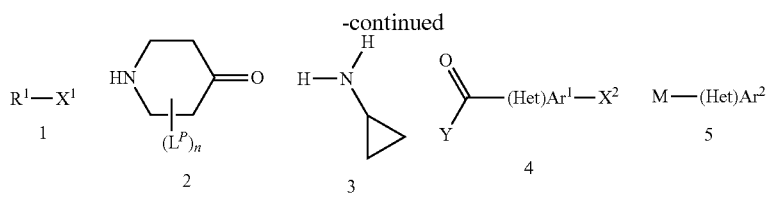

$X^1, X^2, Y$ = leaving group
M = metal or pseudo-metal group

A general way of attaching residue $R^1$ to the N atom of the piperidine of the compounds of the invention (I) or an intermediate towards them is sketched in Scheme 2; $R^1$, $L^P$, and n have the meanings as defined hereinbefore and hereinafter. An $R^1$ group linked via a methylene unit may be attached to the piperidine N by using an $R^1$ group bearing a leaving group at the $CH_2$ unit to be attached, such as Cl, Br, I, $OSO_2C_{1-4}$-alkyl, $OSO_2$aryl, or $OSO_2CF_3$. The substitution is usually done in the presence of a base, e.g. $Na_2CO_3$, $K_2CO_3$, $Cs_2CO_3$, pyridine, triethylamine, ethyldiisopropylamine, or 1,8-diazabicyclo[5.4.0]undec-7-ene, in a solvent such as toluene, tetrahydrofuran, 1,4-dioxane, 1,2-dimethoxyethane, acetonitrile, N,N-dimethylformamide, N,N-dimethylacetamide, N-methylpyrrolidinone, water, methanol, ethanol, isopropanol, dimethyl sulfoxide, or mixtures thereof, at 20 to 220° C. by conventional or microwave heating.

Alternatively, the $CH_2$ moiety of residue $R^1$ is formed during the attachment reaction by reductive alkylation employing $R^1$ as aldehyde and a reducing agent, such as $NaH_3BCN$ or $NaHB(O_2CCH_3)_3$. Using a carboxylic acid derivative of $R^1$ also allows the attachment of $R^1$ via a $CH_2$ unit by employing a two step procedure, amide coupling followed by reduction of the formed amide carbonyl group.

Scheme 2

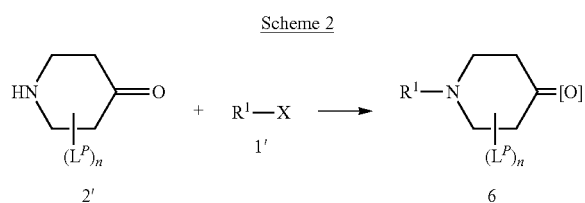

[O] = O or protective group for =O, e.g., $OCH_2CH_2O$
X = leaving group, e.g., F, Cl, Br, I, $OSO_2CF_3$, $OSO_2C_{1-4}$-alkyl, $OSO_2$-aryl, $SO_2C_{1-4}$-alkyl, $NO_2$ The linkage between the piperidine and the cyclopropylamine fragment is preferably established via reductive amination from a piperidinone, such as 6', and cyclopropyl-amine (3) (Scheme 3); $R^1$, $L^P$, and n have the meanings as defined hereinbefore and hereinafter. Suitable reducing agents may be complex metal hydrides, such as sodium borohydride, lithium borohydride, sodium triacetoxyborohydride, or sodium cyano-borohydride, optionally used in combination with an acid, e.g. acetic acid, or hydrogen that is employed in the presence of a transition metal catalyst, e.g. palladium on charcoal or Raney-Ni.

Scheme 3

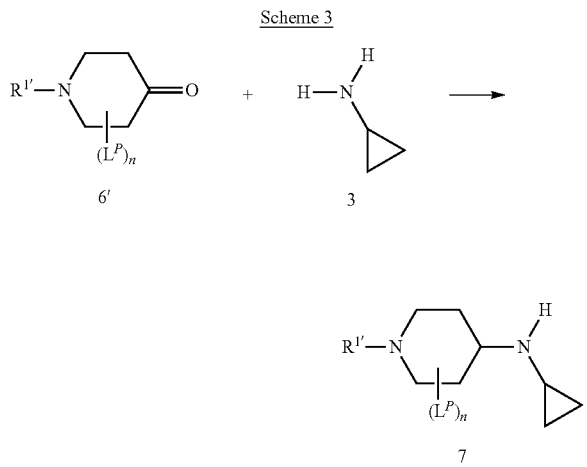

$R^{1'}$ = $R^1$ or protective group, e.g., tBuOC(=O), $PhCH_2OC$(=O), $F_3CC$(=O)

The amide linkage in compounds I or any intermediate towards I of the carboxylic carbon atom and the N bearing the cyclopropyl group is a routine transformation in organic synthesis for which multiple methods and strategies are known (Scheme 4); $R^1$, $L^P$, n, (Het)Ar$^1$, and (Het)Ar$^2$ have the meanings as defined hereinbefore and hereinafter. The carboxylic acid may be transformed into a sufficiently reactive derivative to be coupled with the amine in a separate reaction step or in situ. Suitable derivatives of the carboxylic acid for the former proceeding may be, for example, carboxylic chlorides, fluorides, cyanides, anhydrides, mixed anhydrides, imidazolides, oxy-benzotriazolides, pentafluorophenyl esters, or 4-nitrophenyl esters. In situ activation of the carboxylic acid may be achieved with e.g. 2-(1H-benzotriazol-1-yl)-1,1,3,3-tetramethyluronium tetrafluoroborate or 2-(7-azabenzotriazol-1-yl)-1,1,3,3-tetramethyluronium hexafluorophosphate. The couplings are preferably conducted in the presence of a base, e.g. N,N-diisopropyl-ethylamine, triethylamine, imidazole, pyridine, potassium carbonate or calcium oxide, and/or further additives, such as 4-dimethylaminopyridine or 1-hydroxybenzotriazol, in solvents, preferably selected from tetrahydrofuran, 1,2-dimethoxyethane, ether, 1,4-dioxane, N,N-dimethylformamide, N,N-dimethylacetamide, N-methylpyrrolidinone, acetonitrile, ethyl acetate, dichloromethane, 1,2-dichloroethane, toluene, benzene, hexanes, and mixtures thereof, preferably at −10 to 140° C.

Scheme 4

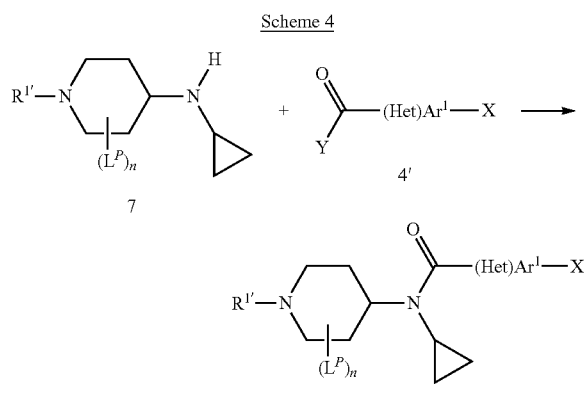

7

8

R¹' = R¹ or protective group, e.g., tBuOC(=O), PhCH₂OC(=O), F₃CC(=O)
X = (Het)Ar² or leaving group, e.g., Cl, Br, I, OSO₂CF₃, OSO₂Me
Y = leaving group, e.g., F, Cl, imidazolide, tBuC(=O)O, iPrC(=O)O, benzotriazol-1-yl-O, pentafluorophenoxy, 4-nitrophenoxy Attaching (Het)Ar² to the (hetero)aromatic ring (Het)Ar¹ in I or an intermediate towards I, e.g. compound 9, may be accomplished as depicted in Scheme 5; (Het)Ar¹ and (H$_{et}$)Ar² have the meanings as defined hereinbefore and hereinafter. Compound 9 is preferably employed as the electrophilic component bearing a leaving group, such as Cl, Br, I, F₃CSO₃, H₃CSO₃, and PhSO₃, and (Het)Ar² as the nucleophilic partner bearing a metal or pseudo metal group, e.g. B(OH)₂, BF₃K, B(OCMe₂CMe₂O), ZnCl, ZnBr, and ZnI. The coupling of the two components is preferably mediated by a transition metal species derived from Fe, Cu, Ni, or Pd. The active catalyst may be a complex of the transition metal with ligands, such as phosphines, e.g. tri-tert-butylphosphine, tri-cyclohexyl-phosphine, optionally substituted biphenyl-dicyclohexylphosphines or biphenyl-di-tert-butylphosphines, 1,1'-bis(diphenylphosphino)-ferrocene, triphenylphosphine, tritolylphosphine, or trifurylphosphine, phosphites, 1,3-disubstituted imdiazole or imidazolidine carbenes, dibenzylideneacetone, allyl or nitriles, an elemental form of the transition metal, such as Pd on carbon or nanoparticles of Fe or Pd, a salt, such as fluoride, chloride, bromide, acetate, triflate or trifluoroacetate, or a combination of the different species mentioned. Depending on the nature of the electrophile and nucleophile additives, such as halide salts, e.g. LiCl, KF, and nBu₄NF, hydroxide sources, e.g. KOH, K₂CO₃, silver salts, such as Ag₂O and Ag(O₃SCF₃)₂, and/or Cu salts, such as copper thiophene-2-carboxylate, may be advantageous or even essential. The coupling is preferably conducted in benzene, toluene, ether, tetrahydrofuran, 1,2-dimethoxy-ethane, 1,4-dioxane, N,N-dimethylformamide, N,N-dimethylacetamide, N-methyl-pyrrolidinone, alcohol, water, or mixtures thereof, at −10 to 180° C. The reactivity of the two building blocks may be reversed, i.e. compound 9 is the nucleophile bearing the metal or pseudo metal residue and (Het)Ar² is the electrophile bearing the leaving group, to access the same products under analogous reaction conditions.

Scheme 5

9      6

W—(Het)Ar¹—(Het)Ar²

10

W = e.g., CN, C(=O)OC$_{1-4}$-alkyl, C(=O)OH, C(=O)OCH₂aryl, C(=O)allyl
X = leaving group, e.g., Cl, Br, I, OSO₂CF₃, OSO₂Me
M = metal group, e.g., B(OH)₂, BF₃K, B(OCMe₂CMe₂O), ZnCl/Br/I, MgCl/Br/I The synthetic routes presented may rely on the use of protecting groups. For example, reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula I", "compound(s) of the invention" and the like denote the compounds of the formula I according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the activation of the G-protein-coupled receptor GPR119 with one or more compounds of the present invention.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or the group to which the substituent is attached.

For example, the term "3-carboxypropyl-group" represents the following substituent:

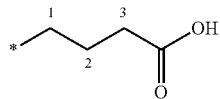

wherein the carboxy group is attached to the third carbon atom of the propyl group. The terms "1-methylpropyl-", "2,2-dimethylpropyl-" or "cyclopropylmethyl-" group represent the following groups:

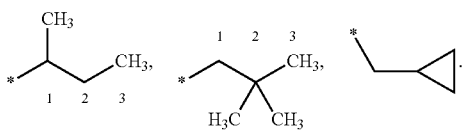

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$" or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo, optical and geometrical isomers (e.g. enantiomers, diastereomers, E/Z isomers etc . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Salts of acids which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example, the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$, The term "$C_{1-n}$-alkylene" wherein n is an integer 1 to n, either alone or in combination with another radical, denotes an acyclic, straight or branched chain divalent alkyl radical containing from 1 to n carbon atoms. For example, the term $C_{1-4}$-alkylene includes $-(CH_2)-$, $-(CH_2-CH_2)-$, $-(CH(CH_3))-$, $-(CH_2-CH_2-CH_2)-$, $-(C(CH_3)_2)-$, $-(CH(CH_2CH_3))-$, $-(CH(CH_3)-CH_2)-$, $-(CH_2-CH(CH_3))-$, $-(CH_2-CH_2-CH_2-CH_2)-$, $-(CH_2-CH_2-CH(CH_3))-$, $-(CH(CH_3)-CH_2-CH_2)-$, $-(CH_2-CH(CH_3)-CH_2)-$, $-(CH_2-C(CH_3)_2)-$, $-(C(CH_3)_2-CH_2)-$, $-(CH(CH_3)-CH(CH_3))-$, $-(CH_2-CH(CH_2CH_3))-$, $-(CH(CH_2CH_3)-CH_2)-$, $-(CH(CH_2CH_2CH_3))-$, $-(CHCH(CH_3)_2)-$ and $-C(CH_3)(CH_2CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes $-CH=CH_2$, $-CH=CH-CH_3$, $-CH_2-CH=CH_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes $-CH=CH-$, $-CH=CH-CH_2-$, $-CH_2-CH=CH-$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes $-C\equiv CH$, $-C\equiv C-CH_3$, $-CH_2-C\equiv CH$.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes $-C\equiv C-$, $-C\equiv C-CH_2-$, $-CH_2-C\equiv C-$.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydro-pentalenyl, octahydroindenyl, decahydronaphthyl, indanyl, tetrahydronaphthyl. Most preferably the term $C_{3-n}$-carbocyclyl denotes $C_{3-n}$-cylcoalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spiro-cyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

The term bicyclic includes spirocyclic.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spiro-carbocyclic, preferably mono-, bi- or spirocyclic-ring system containing one or more heteroatoms selected from N, O or $S(O)_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or $S(O)_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

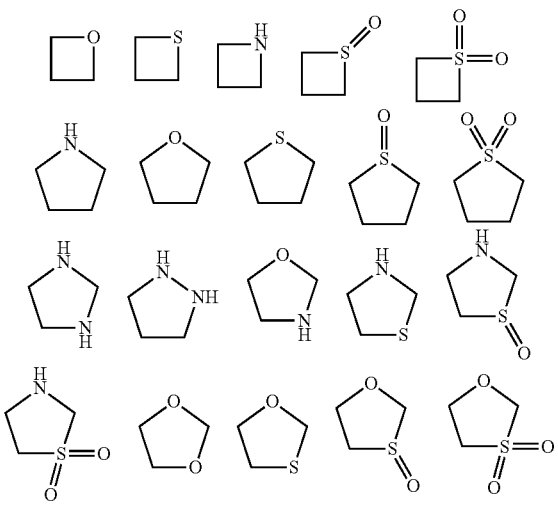

31
-continued
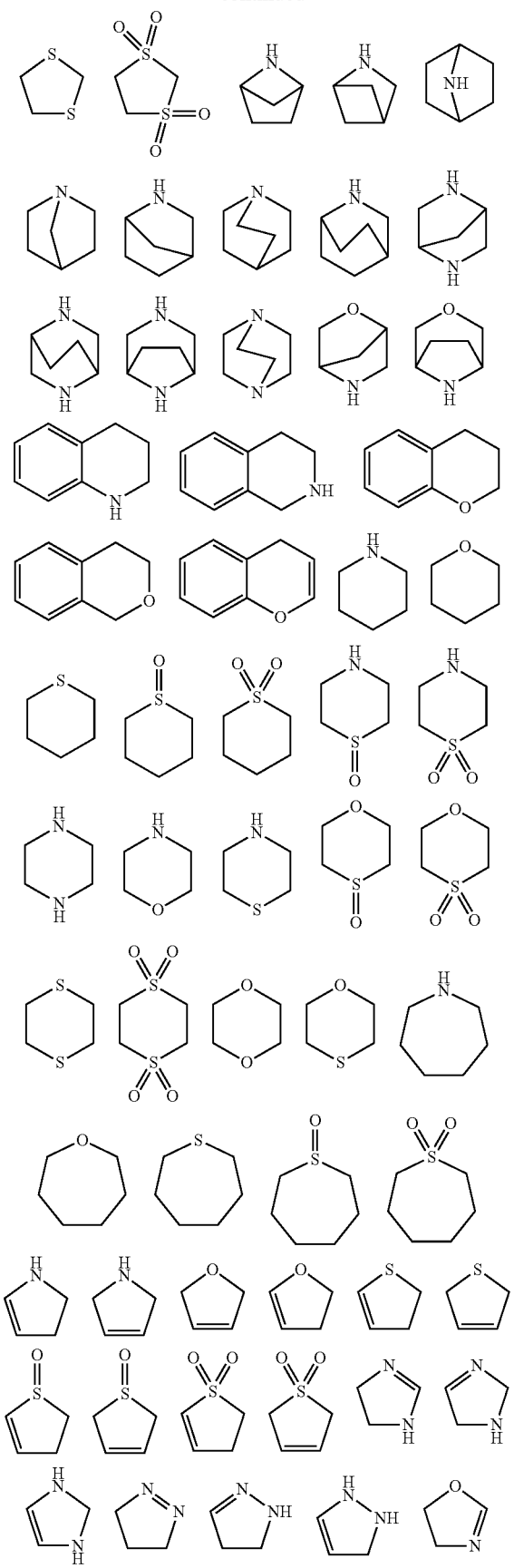
32
-continued
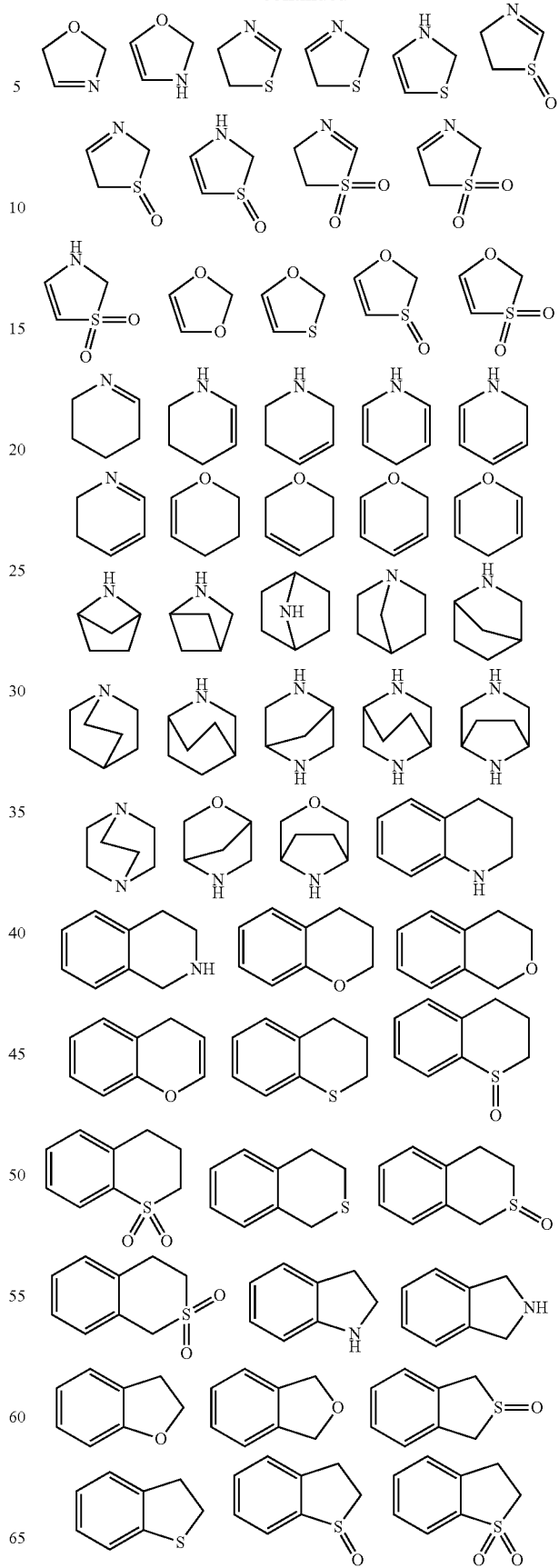

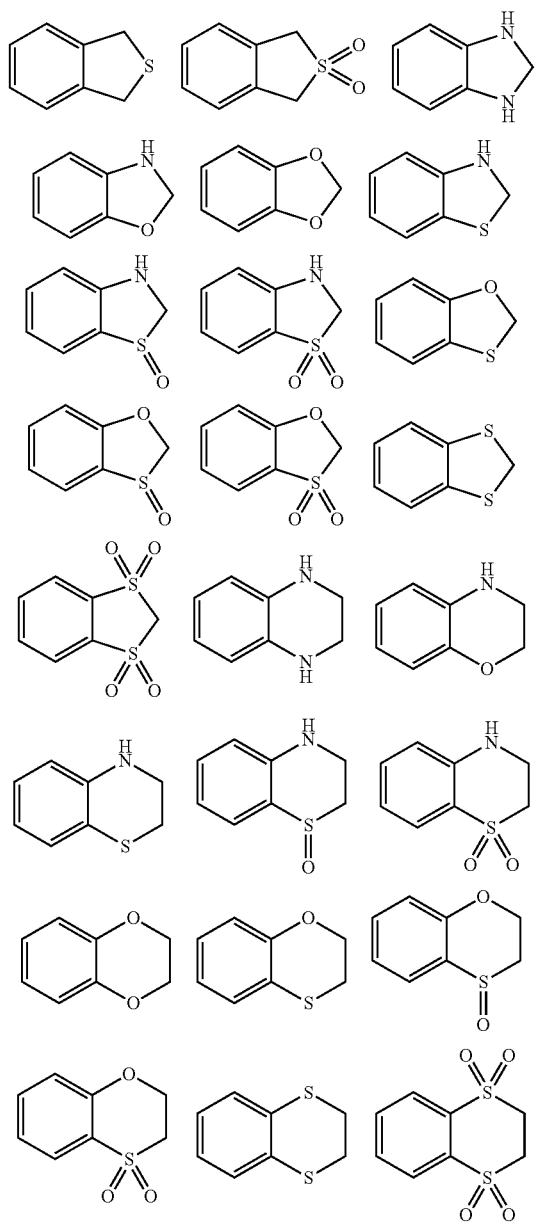

The term "heteroaryl" means a mono- or polycyclic, preferably mono- or bicyclic ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

-continued

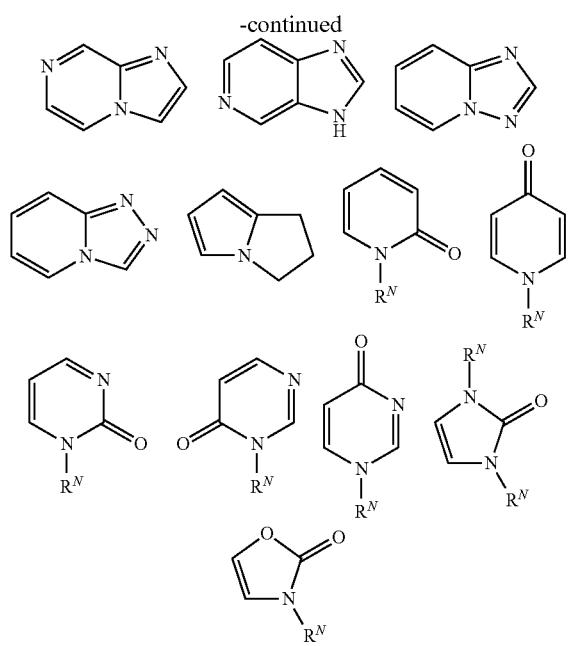

R^N = H or residue attached via a C atom

Many of the terms given above may be used repeatedly in the definition of a formula or group and in each case have one of the meanings given above, independently of one another.

Pharmacological Activity

The activity of the compounds of the invention may be demonstrated using the following assay:

The compounds of formula I according to the invention modulate the activity of the G-protein-coupled receptor GPR119. The effect of the compounds on the activation of GPR119 and on the stimulation of intracellular cAMP concentration is determined using the AlphaScreen cAMP Assay Kit (Cat. No. #6760625R) made by PerkinElmer.

MIN6 cells [Miyazaki Jet al. Endocrinology. 1990 July; 127(1):126-32] are stably transfected with an expression vector for human GPR119 cDNA (Acc. No. NP_848566). Min-6 / hGPR119 cells are cultured in DMEM, 10% FBS, 50 µM β-mercaptoethanol, 0.3 mg/mL Geniticin, 2 mM GlutaMAX at 37° C. 5% CO2. For the assay, the cells are seeded in Optiplates (white, 384-well, 160W-barcoded, TC, sterile with lid, Cat. No. #6007688 (Perkin Elmer); 10000 cells/well; 50 µl). The plates covered with lids are then incubated for 24 hours at 37° C./5% $CO_2$. After the medium is aspirated from the wells completely, 10 µl of the test compound are added, the compounds are diluted using stimulating buffer (140 mM NaCl, 3.6 mM KCl, 0.5 mM $NaH_2PO_4$, 0.5 mM $MgSO_4$, 1.5 mM $CaCl_2$, 10 mM Hepes, 5 mM $NaHCO_3$; pH 7.4. 0.5 mM IBMX and 0.1% BSA, the final DMSO concentration is 1%). After 45 minutes incubation at room temperature (approx. 20° C.), the cAMP concentrations are determined using the AlphaScreen cAMP Assay Kit (Cat.No.# 6760625R from PerkinElmer). 10 µl of Biotin-cAMP (final concentration 1 U/well in lysing buffer (5 mM Hepes (pH 7.4), 0.1% BSA, 0.5% Tween) and 10 µL Bead solution (final concentration 1 U/well in lysing buffer) are added. The plates are incubated for another 2 hours at room temperature. The cAMP concentrations are calculated using a cAMP standard curve from the Alpha Screen Counts. The data analysis is carried out by calculating the $EC_{50}$ value and the maximum value based on a positive control, using suitable software (Graphpad Prism). The compounds according to the invention increase the intracellular cAMP level in the range of 3-5.

The compounds according to the invention typically have $EC_{50}$ values in the range from about 1 nM to about 10 µM, preferably from 1 nM to 1 µM, preferably less than 1 µM, particularly preferably less than 500 nM, most particularly preferably less than 100 nM.

$EC_{50}$ values (cAMP assay) for compounds according to the invention are shown in the following table. The number of the compound corresponds to the number of the Example in the experimental section.

| Example No. | $EC_{50}$ [nM] | Example No. | $EC_{50}$ [nM] | Example No. | $EC_{50}$ [nM] | Example No. | $EC_{50}$ [nM] |
|---|---|---|---|---|---|---|---|
| 1 | 456 | 2 | 643 | 3 | 79 | 4 | 63 |
| 5 | 27 | 6 | 50 | 7 | 9 | 8 | 22 |
| 9 | 6 | 10 | 19 | 13 | 2 | | |

Alternatively, the effect of the compounds on the activation of GPR119 are determined as follows:

Quantitative detection of cAMP accumulation from cells expressing human GPR119 receptor is achieved using Perkin Elmer's LANCE cAMP-384 Kit (Cat #AD0264) according to the manufacturer's protocol. Briefly, HEK293 cells stably expressing a mutant form of the human GPR119 receptor as assay tool (Methionine 1 replaced with the amino acid sequence MKTIIALSYIFCLVFADYKDDDDA, and T327 & S329 changed to alanines; SEQ ID No. 1) are grown to 50-70% confluency in cell culture media (DMEM, 10% heat inactivated Fetal Bovine Serum, 50 I.U./mL penicillin, 50 µg/mL streptomycin, 10 mM HEPES, 20 µg/mL G418 Sulfate). On the day of the assay, GPR119 stable HEK293 cells are lifted from the tissue culture plate and 1000 cells/well are incubated along with various concentrations of test compounds for 20 min at 37+ C. Detection Buffer (50mM HEPES, 10mM calcium chloride, 0.35% Triton X-100, 1 mg/mL BSA) containing cAMP-specific antibody is then added to all wells and allowed to equilibrate in the dark for 10 minutes at room temperature. Upon equilibration, Detection Buffer containing europium-labeled cAMP tracer complex is added to all wells and allowed to react for 1 hour at room temperature. After 1 hour, bound europium-labeled cAMP tracer is measured using a Perkin Elmer Envision plate reader. The quantity of cAMP generated in each well is derived from a standard curve. $EC_{50}$ is determined using nonlinear regression analysis of the cAMP values over a range of agonist concentration (12 points spanning the range from 30 µM to 100 pM).

$EC_{50}$ values (determined as described above) for compounds according to the invention are shown in the following table. The number of the compound corresponds to the number of the Example in the experimental section.

| Example No. | $EC_{50}$ [nM] | Example No. | $EC_{50}$ [nM] | Example No. | $EC_{50}$ [nM] | Example No. | $EC_{50}$ [nM] |
|---|---|---|---|---|---|---|---|
| 11 | 10 | 12 | 12 | 14 | 27 | 15 | 30 |

In view of their ability to modulate the activity of the G-protein-coupled receptor GPR119, in particular an agonistic activity, the compounds of general formula I according to the invention, including the corresponding salts thereof, are theoretically suitable for the treatment of all those diseases or conditions which may be affected or which are mediated by the activation of the G-protein-coupled receptor GPR119.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR119 in a patient, preferably in a human.

In yet another aspect the present invention relates to a method for treating a disease or condition mediated by the activation of the G-protein-coupled receptor GPR119 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR119 embrace metabolic diseases or conditions.

According to one aspect the compounds and pharmaceutical compositions of the present invention are particularly suitable for treating diabetes mellitus, in particular Type 2 diabetes, Type 1 diabetes, complications of diabetes (such as e.g. retino-pathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmacuetical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, athero-sclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2 inhibitors, insulin and insulin analogues, GLP-1 and GLP-1 analogues or amylin and amylin analogues, cycloset, 11β-HSD1 inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to ¹⁄₁ of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR119, in particular diseases or conditions as described hereinbefore and hereinafter.

In yet another aspect the present invention relates to a method for treating a disease or condition mediated by the activation of the G-protein-coupled receptor GPR119 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm. The terms "ambient temperature" and "room temperature" are used interchangeably and designate a temperature of about 20° C.

Parameters of analytical HPLC employed for characterization of products (TFA denotes trifluoroacetic acid):

| Method: | 1 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Methanol] | Flow [ml/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method: | 2 |
|---|---|
| Device: | Agilent 1100 with DA and MS detector |
| Column: | XBridge C18, 4.6 × 30 mm, 3.5 μm |
| Column Supplier: | Waters |

| Gradient/ Solvent Time [min] | % Solvent [H$_2$O, 0.1% HCOOH] | % Solvent [Methanol] | Flow [ml/min] | Temperature [° C.] |
|---|---|---|---|---|
| 0.0 | 95 | 5 | 4 | 60 |
| 0.15 | 95 | 5 | 4 | 60 |
| 1.70 | 0 | 100 | 4 | 60 |
| 2.25 | 0 | 100 | 4 | 60 |

| Method: | 3 |
|---|---|
| Device: | Agilent 1100 with DA and MS detector |
| Column: | XBridge C18, 4.6 × 30 mm, 3.5 μm |
| Column Supplier: | Waters |

| Gradient/ Solvent Time [min] | % Solvent [H$_2$O, 0.1% NH$_3$] | % Solvent [Methanol] | Flow [ml/min] | Temperature [° C.] |
|---|---|---|---|---|
| 0.0 | 95 | 5 | 4 | 60 |
| 0.15 | 95 | 5 | 4 | 60 |
| 1.70 | 0 | 100 | 4 | 60 |
| 2.25 | 0 | 100 | 4 | 60 |

| Method: | 4 |
|---|---|
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [Methanol] | Flow [ml/min] | Temperature [° C.] |
|---|---|---|---|---|
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method: | 5 |
|---|---|
| Device: | Agilent 1200 with DA and MS detector |
| Column: | Sunfire, 3 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [ml/min] | Temperature [° C.] |
|---|---|---|---|---|
| 0.0 | 97 | 35 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 6 |
|---|---|
| Device: | Berger/Thar/Waters Multi-gram II prep SFC system with UV detection |
| Column: | Chiralcel AD-H, 21 × 250 mm, 5 μm |
| Column Supplier: | Chiral Technologies |

| Gradient/ Solvent Time [min] | % Solvent [CO$_2$] | % Solvent [EtOH + 0.5% N,N-dimethyl-ethylamine] | Flow [ml/min] | Temperature [° C.] |
|---|---|---|---|---|
| 0.00 | 90 | 10 | 65 | 30 |
| 15 | 90 | 10 | 65 | 30 |

| Method: | 7 |
|---|---|
| Column: | MAX-RP, 2 × 50 mm |
| Column Supplier: | Phenomenex Gemini |

| Gradient/ Solvent Time [min] | % Solvent [H$_2$O, 0.025% TFA] | % Solvent [Acetonitrile, 0.025% TFA] | Flow [ml/min] | Temperature [° C.] |
|---|---|---|---|---|
| 0.00 | 95 | 5 | 1.0 | 30 |
| 2.50 | 10 | 90 | 1.0 | 30 |
| 3.50 | 10 | 90 | 1.0 | 30 |

| Method: | 8 |
|---|---|
| Column: | NX C18, 3 × 100 mm, 5 μm |
| Column Supplier: | Phenomenex Gemini |

| Gradient/ Solvent Time [min] | % Solvent [H$_2$O, 0.04% NH$_4$OH] | % Solvent [Acetonitrile, 0.04% NH$_4$OH] | Flow [ml/min] | Temperature [° C.] |
|---|---|---|---|---|
| 0.00 | 95 | 5 | 2.0 | 30 |
| 5.20 | 5 | 95 | 2.0 | 30 |

Intermediate 1

N-Cyclopropyl-4-oxazol-5-yl-N-piperidin-4-yl-benzamide

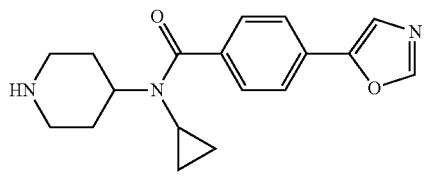 [SMILES: O=C(c1ccc(-c2cnco2)cc1)N(C1CCNCC1)C1CC1]

2-(1H-Benzotriazol-1-yl)-1,1,3,3-tetramethyluronium tetrafluoroborate (6.10 g) is added to a solution of 4-oxazol-5-yl-benzoic acid (3.00 g) and ethyldiisopropylamine (5.56 mL) in N,N-dimethylformamide (50 mL) at room temperature. The solution is stirred for 10 min prior to the addition of 4-cyclopropylamino-piperidine-1-carboxylic acid tert-butyl ester (4.57 g). The resulting mixture is kept at room temperature over night. The mixture is treated with activated charcoal and filtered through a pad of basic aluminum oxide. The pad is washed with N,N-dimethylformamide/methanol (9:1) and the combined filtrates are concentrated in vacuo. The residue is dissolved in 1,4-dioxane (35 mL), a 4 M solution of hydrogen chloride in 1,4-dioxane (20 mL) is added and the resulting mixture is stirred at room temperature for 2 h. The solvent is evaporated and the residue is taken up in water. The resulting mixture is washed with dichloromethane, basified with NaOH solution and extracted with dichloromethane.

The combined extracts are dried over Na$_2$SO$_4$ and concentrated in vacuo. The residue is triturated with diethyl ether to afford the title compound. LC (method 1): $t_R$=0.70 min; Mass spectrum (ESI⁺): m/z=312 [M+H]⁺.

Intermediate 2

N-Cyclopropyl-N-[1-(2-hydroxy-2-methyl-propyl)-piperidin-4-yl]-4-oxazol-5-yl-benzamide

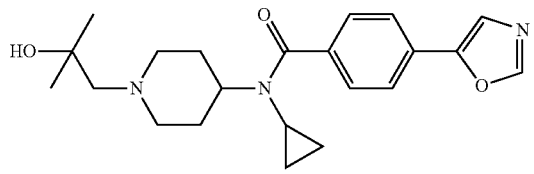 [SMILES: CC(C)(O)CN1CCC(N(C(=O)c2ccc(-c3cnco3)cc2)C2CC2)CC1]

1,1-Dimethyloxirane (88 µL) is added to N-cyclopropyl-4-oxazol-5-yl-N-piperidin-4-yl-benzamide (100 mg) in methanol (5 mL). The mixture is stirred for 4 h at room temperature and at 50° C. over night. Since the conversion is still incomplete, another portion of 1,1-dimethyloxirane (88 µL) is added and the mixture is stirred for 8 h at 50° C. The reaction mixture is diluted with water (10 mL) and stirred for 1 h at room temperature. The precipitate is filtered off and washed with water and t-butyl methylether to give the title compound. LC (method 2): $t_R$=1.00 min; Mass spectrum (ESI⁺): m/z=384 [M+H]⁺.

Intermediate 3

N-Cyclopropyl-3-fluoro-4-oxazol-5-yl-N-piperidin-4-yl-benzamide

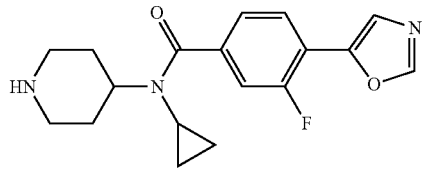 [SMILES: O=C(c1ccc(-c2cnco2)c(F)c1)N(C1CCNCC1)C1CC1]

The title compound is prepared from 3-fluoro-4-oxazol-5-yl-benzoic acid and 4-cyclopropylamino-piperidine-1-carboxylic acid tert-butyl ester following a procedure analogous to that described for Intermediate 1. The deprotection step is accomplished by using trifluoroacetic acid in dichloromethane. LC (method 2): $t_R$=0.98 min; Mass spectrum (ESI⁺): m/z=330 [M+H]⁺.

Intermediate 4

N-Cyclopropyl-3-fluoro-N-[1-(2-hydroxy-2-methyl-propyl)-piperidin-4-yl]-4-oxazol-5-yl-benzamide

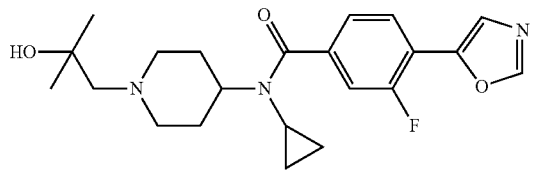 [SMILES: CC(C)(O)CN1CCC(N(C(=O)c2ccc(-c3cnco3)c(F)c2)C2CC2)CC1]

The title compound is prepared from N-cyclopropyl-3-fluoro-4-oxazol-5-yl-N-piperidin-4-yl-benzamide and 1,1-dimethyloxirane following a procedure analogous to that described for Intermediate 2. LC (method 2): $t_R$=0.98 min; Mass spectrum (ESI⁺): m/z=402 [M+H]⁺.

Intermediate 5

5-(4-Cyano-phenyl)-isoxazole-3-carboxylic acid

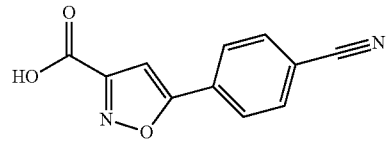 [SMILES: N#Cc1ccc(-c2cc(C(=O)O)no2)cc1]

A mixture of 5-(4-cyano-phenyl)-isoxazole-3-carboxylic acid ethyl ester (100 mg) and 1 N aqueous NaOH solution (1.24 mL) in tetrahydrofuran (4.5 mL) is stirred at room temperature for 3 h. The reaction mixture is acidified with 3 N hydrochloric acid and concentrated in vacuo. The residue is triturated with water; the precipitate is filtered off and dried to give the title compound. LC (method 3): $t_R$=1.01 min; Mass spectrum (ESI⁺): m/z=215 [M+H]⁺.

Intermediate 6

4-{[5-(4-Cyano-phenyl)-isoxazole-3-carbonyl]-cyclopropyl-amino}-piperidine-1-carboxylic acid tert-butyl ester

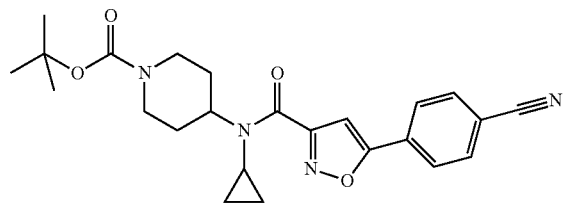 [SMILES: CC(C)(C)OC(=O)N1CCC(N(C(=O)c2cc(-c3ccc(C#N)cc3)on2)C2CC2)CC1]

Oxalyl chloride (137 µL) is added drop wise to a cooled solution of 5-(4-cyano-phenyl)-isoxazole-3-carboxylic acid (88 mg) in dichloromethane (5 mL). One drop of N,N-dimethylformamide is added and the mixture is stirred at room temperature for 1 h. The reaction mixture is concentrated in vacuo and the crude 5-(4-cyano-phenyl)-isoxazole-3-carbonyl chloride is dissolved in tetrahydrofuran (5 mL). 4-cyclopropylamino-piperidine-1-carboxylic acid tert-butyl ester (99 mg) and triethylamine (114 µL) are added and the resulting mixture is stirred at room temperature over night. The reaction mixture is concentrated in vacuo and the residue is chromatographed on silica gel (cyclohexane/ethyl acetate 50:50→0:100). The crude product is triturated with diethyl ether, filtered off, and dried to give the title compound. LC (method 3): $t_R$=1.69 min; Mass spectrum (ESI⁺): m/z=437 [M+H]⁺.

Intermediate 7

5-(4-Cyano-phenyl)-isoxazole-3-carboxylic acid cyclopropyl-piperidin-4-yl-amide

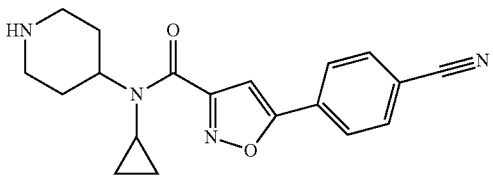 [SMILES: N#Cc1ccc(-c2cc(C(=O)N(C3CCNCC3)C3CC3)no2)cc1]

A mixture of 4-{[5-(4-cyano-phenyl)-isoxazole-3-carbonyl]-cyclopropyl-amino}-piperidine-1-carboxylic acid tert-butyl ester (90 mg) and trifluoroacetic acid (0.20 mL) in dichloromethane (3 mL) is stirred for 3 h at room temperature. The reaction mixture is diluted with dichloromethane prior to the addition of 2 N aqueous NaOH solution (1.5 mL) and aqueous $Na_2CO_3$ solution. The resulting mixture is stirred vigorously for 10 min. The organic phase is separated and the aqueous phase is extracted with dichloromethane. The combined extracts are dried over $MgSO_4$ and concentrated in vacuo to give the desired product. LC (method 4): $t_R$=1.02 min; Mass spectrum (ESI+): m/z=337 [M+H]$^+$.

Intermediate 8

5-(4-Cyano-phenyl)-isoxazole-3-carboxylic acid cyclopropyl-[1-(2-hydroxy-2-methyl-propyl)-piperidin-4-yl]-amide

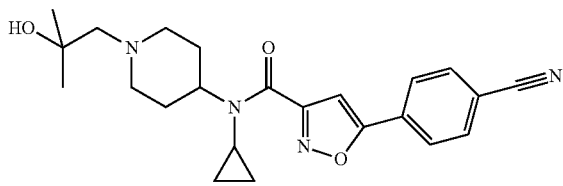 [SMILES: CC(C)(O)CN1CCC(N(C(=O)c2cc(-c3ccc(C#N)cc3)on2)C2CC2)CC1]

The title compound is prepared from 5-(4-cyano-phenyl)-isoxazole-3-carboxylic acid cyclopropyl-piperidin-4-yl-amide and 1,1-dimethyloxirane following a procedure analogous to that described for Intermediate 2. LC (method 4): $t_R$=1.17 min; Mass spectrum (ESI+): m/z=409 [M+H]$^+$.

Intermediate 9

3-(4-Cyano-2-fluoro-phenyl)-5-methoxy-4,5-dihydro-isoxazole-5-carboxylic acid methyl ester

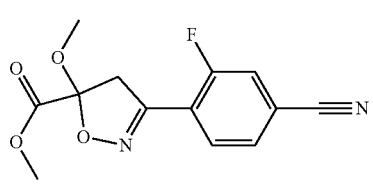

Triethylamine (1.05 mL) is added drop wise to a mixture of (4-cyano-2-fluoro-benzaldehyde chlorooxime (600 mg) and 2-methoxyacrylate (421 mg) in dichloromethane (7.5 mL). The reaction mixture is stirred over night at room temperature. Water is added and the aqueous phase is extracted with ethyl acetate. The combined organic phases are washed with brine, dried over $MgSO_4$, and concentrated in vacuo. The residue is chromatographed on silica gel (cyclohexane/ethyl acetate 80:20→50:50) to afford the title compound. LC (method 4): $t_R$=0.93 min; Mass spectrum (ESI+): m/z=279 [M+H]$^+$.

Intermediate 10

3-(4-Cyano-2-fluoro-phenyl)-isoxazole-5-carboxylic acid

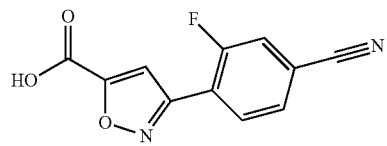 [SMILES: N#Cc1ccc(-c2cc(C(=O)O)on2)c(F)c1]

A mixture of 3-(4-cyano-2-fluoro-phenyl)-5-methoxy-4,5-dihydro-isoxazole-5-carboxylic acid methyl ester (172 mg), 1N aqueous NaOH solution (2 mL), and tetrahydrofuran (5 mL) is stirred at room temperature for 3 h. The reaction mixture is acidified with 1 N hydrochloric acid (approximately pH 3) and concentrated in vacuo.

The residue is triturated with water and the precipitate is filtered off and dried to give the title compound. LC (method 4): $t_R$=0.38 min; Mass spectrum (ESI−): m/z=231 [M−H]$^-$.

Intermediate 11

4-{[3-(4-Cyano-2-fluoro-phenyl)-isoxazole-5-carbonyl]-cyclopropyl-amino}-piperidine-1-carboxylic acid tert-butyl ester

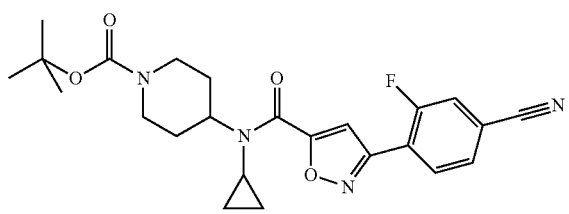 [SMILES: CC(C)(C)OC(=O)N1CCC(N(C(=O)c2cc(-c3ccc(C#N)cc3F)no2)C2CC2)CC1]

The title compound is prepared from 3-(4-cyano-2-fluoro-phenyl)-isoxazole-5-carboxylic acid and 4-cyclopropylamino-piperidine-1-carboxylic acid tert-butyl ester following a procedure analogous to that described for Intermediate 6. LC (method 4): $t_R$=1.27 min; Mass spectrum (ESI+): m/z=455 [M+H]$^+$.

Intermediate 12

3-(4-Cyano-2-fluoro-phenyl)-isoxazole-5-carboxylic acid cyclopropyl-piperidin-4-yl-amide

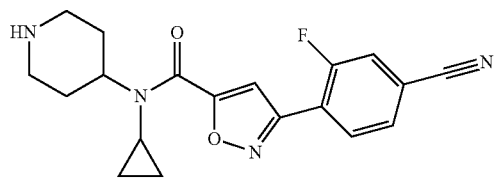 [SMILES: N#Cc1ccc(-c2cc(C(=O)N(C3CCNCC3)C3CC3)on2)c(F)c1]

The title compound is prepared from 4-{[3-(4-cyano-2-fluoro-phenyl)-isoxazole-5-carbonyl]-cyclopropyl-amino}-piperidine-1-carboxylic acid tert-butyl ester following a procedure analogous to that described for Intermediate 7. LC (method 4): $t_R$=1.03 min; Mass spectrum (ESI⁺): m/z=355 [M+H]⁺.

Intermediate 13

3-(4-Cyano-2-fluoro-phenyl)-isoxazole-5-carboxylic acid cyclopropyl-[1-(2-hydroxy-2-methyl-propyl)-piperidin-4-yl]-amide

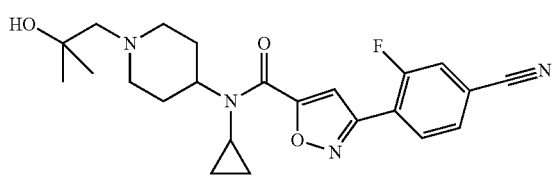 [SMILES: CC(C)(O)CN1CCC(N(C(=O)c2cc(-c3ccc(C#N)cc3F)no2)C2CC2)CC1]

The title compound is prepared from 3-(4-cyano-2-fluoro-phenyl)-isoxazole-5-carboxylic acid cyclopropyl-piperidin-4-yl-amide and 1,1-dimethyloxirane following a procedure analogous to that described for Intermediate 2. LC (method 4): $t_R$=1.19 min; Mass spectrum (ESI⁺): m/z=427 [M+H]⁺.

Intermediate 14

5-(4-Cyano-2-fluoro-phenyl)-isoxazole-3-carboxylic acid ethyl ester

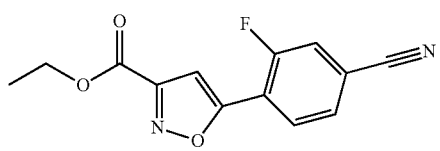 [SMILES: CCOC(=O)c1cc(-c2ccc(C#N)cc2F)on1]

A mixture of 5-chloro-isoxazole-3-carboxylic acid ethyl ester (600 mg), 4-cyano-2-fluorophenylboronic acid (665 mg), and aqueous $Na_2CO_3$ solution (2 M; 4.41 mL) in 1,4-dioxane (15 mL) is purged with argon for 15 min prior to the addition of Pd(PPh₃)₄ (276 mg). The reaction mixture is heated under an argon atmosphere to 140° C. for 20 min in a microwave oven. The solvent is evaporated in vacuo and the residue is mixed with water and ethyl acetate. The aqueous phase is extracted with ethyl acetate and the combined extracts are washed with brine, dried over MgSO₄ and concentrated in vacuo. The crude product is purified by silica gel chromatography (cyclohexane/ethyl acetate 80:20→50:50). LC (method 3): $t_R$=1.50 min; Mass spectrum (ESI+): m/z=261 [M+H]⁺.

Intermediate 15

5-(4-Cyano-2-fluoro-phenyl)-isoxazole-3-carboxylic acid

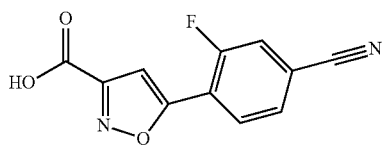 [SMILES: N#Cc1ccc(-c2cc(C(=O)O)no2)c(F)c1]

The title compound is prepared from 5-(4-cyano-2-fluoro-phenyl)-isoxazole-3-carboxylic acid ethyl ester by treatment with aqueous NaOH solution in tetrahydrofuran. LC (method 4): $t_R$=0.32 min; Mass spectrum (EI): m/z=232 [M]⁺.

Intermediate 16

4-{[5-(4-Cyano-2-fluoro-phenyl)-isoxazole-3-carbonyl]-cyclopropyl-amino}-piperidine-1-carboxylic acid tert-butyl ester

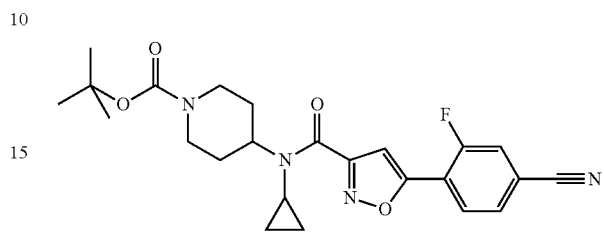

The title compound is prepared from 5-(4-cyano-2-fluoro-phenyl)-isoxazole-3-carboxylic acid and 4-cyclopropylamino-piperidine-1-carboxylic acid tert-butyl ester following a procedure analogous to that described for Intermediate 6. LC (method 3): $t_R$=1.69 min; Mass spectrum (ESI⁻): m/z=453 [M−H]⁻.

Intermediate 17

5-(4-Cyano-2-fluoro-phenyl)-isoxazole-3-carboxylic acid cyclopropyl-piperidin-4-yl-amide

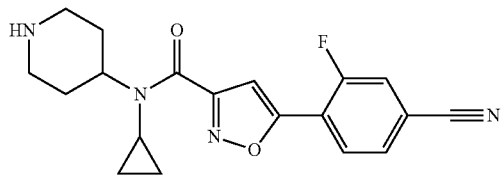 [SMILES: N#Cc1ccc(-c2cc(C(=O)N(C3CCNCC3)C3CC3)no2)c(F)c1]

The title compound is prepared from 4-{[5-(4-cyano-2-fluoro-phenyl)-isoxazole-3-carbonyl]-cyclopropyl-amino}-piperidine-1-carboxylic acid tert-butyl ester following a procedure analogous to that described for Intermediate 7. LC (method 3): $t_R$=1.18 min; Mass spectrum (ESI⁺): m/z=355 [M+H]⁺.

Intermediate 18

5-(4-Cyano-2-fluoro-phenyl)-isoxazole-3-carboxylic acid cyclopropyl[1-(2-hydroxy-2-methyl-propyl)-piperidin-4-yl]-amide

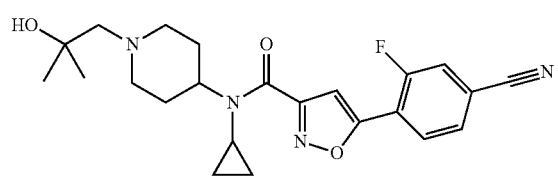 [SMILES: CC(C)(O)CN1CCC(N(C(=O)c2cc(-c3ccc(C#N)cc3F)on2)C2CC2)CC1]

The title compound is prepared from 5-(4-cyano-2-fluoro-phenyl)-isoxazole-3-carboxylic acid cyclopropyl-piperidin-4-yl-amide and 1,1-dimethyloxirane following a procedure analogous to that described for Intermediate 2. LC (method 3): $t_R$=1.21 min; Mass spectrum (ESI$^+$): m/z=427 [M+H]$^+$.

Intermediates 19 and 20

Benzyl (3R,4S)-4-(cyclopropylamino)-3-fluoropiperidine-1-carboxylate arbitrarily assigned as Isomer 1 (first eluting) and Benzyl (3S,4R)-4-(cyclopropylamino)-3-fluoropiperidine-1-carboxylate arbitrarily assigned as Isomer 2 (second eluting)

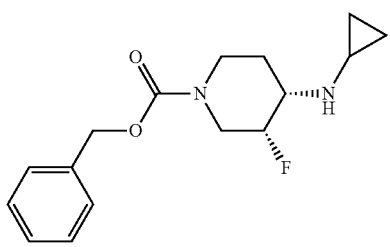

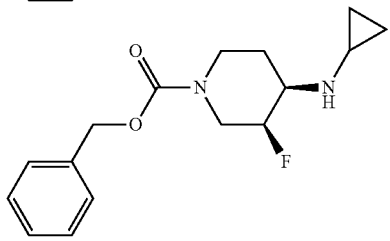

To a solution of benzyl-3-fluoro-4-oxopiperidine-1-carboxylate (10.0 g) and cyclopropylamine (2.5 g) in dichloromethane (100 mL) are added sodium triacetoxyborohydride (10.1 g) and glacial acetic acid (5.0 g). The reaction mixture is stirred at room temperature for 20 h. Then 60 mL of 2 N NaOH is added to reach pH 10. The mixture is extracted with dichloromethane (2×50 mL). The combined organic phases are dried over sodium sulfate, filtered and concentrated in vacuo and purified by silica gel chromatography (dichloromethane/methanol 90:10) to afford the desired product as a mixture of mainly cis isomers [LC (method 20): $t_R$=1.98 min; mass spectrum (APCI): m/z=293 [M+H]$^+$]. Chiral SFC separation (chiral SFC method 6) gives the separated title compounds (cis isomers of unknown absolute stereochemistry) arbitrarily assigned as Isomer 1 (first eluting; 7.25 min) and Isomer 2 (second eluting; 9.41 min).

Intermediate 21 tert-Butyl N-cyclopropyl-N-[(3R,4S)-3-fluoropiperidin-4-yl]carbamate

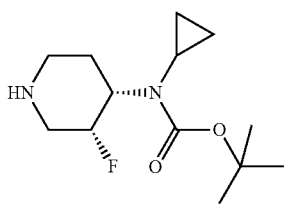 [SMILES: CC(C)(C)OC(=O)N(C1CC1)[C@H]1CCNC[C@H]1F]

Benzyl (3R,4S)-4-(cyclopropylamino)-3-fluoropiperidine-1-carboxylate (arbitrarily assigned as Isomer 1) (3.0 g) is dissolved in 1:1 tetrahydrofuran/water (100 mL) and NaOH (800 mg, 20 mmol) is added followed by di-tert-butyl dicarbonate (2.6 g) and stirred rapidly at room temperature overnight. The reaction is heated to reflux and additional portions of di-tert-butyl dicarbonate are added over two days (3×2.6 g). The reaction is extracted with ethyl acetate and the organic extracts are washed with brine, dried over MgSO$_4$ and concentrated. Chromatography on silica gel eluting with ethyl acetate/hexane gives the Boc-protected intermediate and elution with methanol/dichloromethane gives recovered amine. The intermediate is re-dissolved in ethyl acetate (30 mL) and 10% Pd/C (200 mg) is added and the reaction mixture stirred under a hydrogen atmosphere for 2 h at room temperature. Filtration through celite and concentration gives the title compound. LC (method 7): $t_R$=1.95 min; Mass spectrum (APCI): m/z=259 [M+H]$^+$.

Intermediate 22 tert-Butyl N-cyclopropyl-N-[(3S,4R)-3-fluoropiperidin-4-yl]carbamate

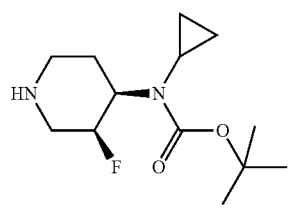 [SMILES: CC(C)(C)OC(=O)N(C1CC1)[C@@H]1CCNC[C@@H]1F]

The title compound is prepared from benzyl (3S,4R)-4-(cyclopropylamino)-3-fluoropiperidine-1-carboxylate (arbitrarily assigned as Isomer 2) following a procedure analogous to that described for Intermediate 21. LC (method 7): $t_R$=2.02 min; Mass spectrum (APCI): m/z=259 [M+H]$^+$.

Intermediate 23

3S,4R)-N-Cyclopropyl-3-fluoro-1-[1-(trifluoromethyl-cyclopropylmethyl)-piperidin-4-amine

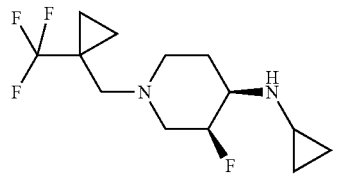 [SMILES: F[C@H]1CN(CC2(C(F)(F)F)CC2)CC[C@H]1NC1CC1]

tert-butyl N-cyclopropyl-N-[(3S,4R)-3-fluoropiperidin-4-yl]carbamate (Intermediate 22, 0.15 g), triethylamine (0.14 mL), 1-(trifluoromethyl)cyclopropane-1-carboxylic acid (0.14 g) and 1-hydroxybenzotriazole (0.1 g) are combined in 1,2-dichloroethane (4 mL) and 1-ethyl-3-(3-dimethylaminopropyl)-carbodiimide (0.17 g) is added and stirred at room temperature overnight. Water is added and the organic phase is separated and dried over MgSO$_4$ and concentrated. The crude amide is purified by chromatography on silica gel eluting with acetone/hexane and after concentration dissolved in 20% trifluoroacetic acid/dichloromethane and stirred at room temperature for 1 h. After concentration dichloromethane (10 mL) and NaOH (2 M, 2 mL) is added and the aqueous layer separated and dried over MgSO$_4$ and concentrated. The crude material is dissolved in diethyl ether and lithium aluminium hydride (30 mg) is added at room temperature and stirred for 1 h. Methanol (0.1 mL) is added followed by ethyl acetate (10 mL) and the mixture is filtered through celite and concentrated in vacuo to give the title compound. LC (method 7): $t_R$=0.50 min; Mass spectrum (APCI): m/z=281 [M+H]$^+$.

Example 1

N-Cyclopropyl-N-[1-(2-fluoro-2-methyl-propyl)-piperidin-4-yl]-4-oxazol-5-yl-benzamide

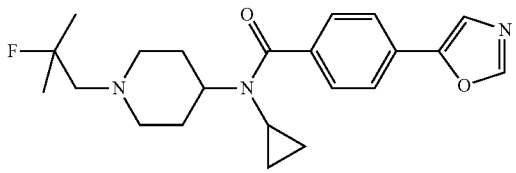 [SMILES: CC(C)(F)CN1CCC(N(C(=O)c2ccc(-c3cnco3)cc2)C2CC2)CC1]

Diethylaminosulfur trifluoride (57 µL) is added drop wise to N-cyclopropyl-N-[1-(2-hydroxy-2-methyl-propyl)-piperidin-4-yl]-4-oxazol-5-yl-benzamide (83 mg) in dry dichloromethane (12 mL) at −78° C. and the reaction mixture is stirred at this temperature for 2 h. The mixture is poured on aqueous NaHCO$_3$ solution (15 mL) and the aqueous phase is extracted with dichloromethane. The combined extracts are washed with brine, dried over MgSO$_4$ and concentrated in vacuo. The solid residue is triturated with diisopropyl ether, filtered off, and dried to give the title compound. LC (method 2): $t_R$=1.10 min; Mass spectrum (ESI$^+$): m/z =386 [M+H]$^+$.

Example 2

N-Cyclopropyl-4-oxazol-5-yl-N-[1-(3,3,3-trifluoro-propyl)-piperidin-4-yl]-benzamide

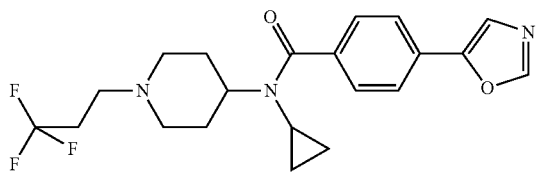 [SMILES: O=C(c1ccc(-c2cnco2)cc1)N(C1CC1)C1CCN(CCC(F)(F)F)CC1]

A mixture of N-cyclopropyl-N-[1-(2-hydroxy-2-methyl-propyl)-piperidin-4-yl]-4-oxazol-5-yl-benzamide (80 mg), 1-iodo-3,3,3-trifluoropropane (108 mg), and K$_2$CO$_3$ (63 mg) in N-methyl-2-pyrrolidone (2 mL) is stirred at room temperature for 4 h and then at 60° C. over night. Since conversion of starting material is still incomplete, K$_2$CO$_3$ (63 mg) and two portions of 1-iodo-3,3,3-trifluoropropane (54 mg each) are added while stirring the reaction mixture for two more days at 80° C. Water is added to the reaction mixture and the aqueous phase is extracted with ethyl acetate. The combined extracts are washed with brine dried over MgSO$_4$ and concentrated in vacuo. The residue is chromatographed on silica gel (cyclohexane/ethyl acetate 75:25→50:50). The crude product is triturated with diethyl ether, filtered off, and dried to give the title compound. LC (method 3): $t_R$=1.08 min; Mass spectrum (ESI$^+$): m/z=408 [M+H]$^+$.

Example 3

N-Cyclopropyl-4-oxazol-5-yl-N-[1-(1-trifluoromethyl-cyclopropylmethyl)-piperidin-4-yl]-benzamide

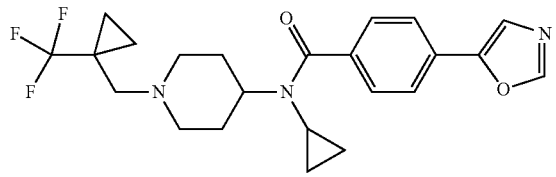 [SMILES: O=C(c1ccc(-c2cnco2)cc1)N(C1CC1)C1CCN(CC2(C(F)(F)F)CC2)CC1]

A mixture of N-cyclopropyl-N-[1-(2-hydroxy-2-methyl-propyl)-piperidin-4-yl]-4-oxazol-5-yl-benzamide (80 mg), methanesulfonic acid (1-trifluoromethyl-cyclopropyl)methyl ester (269 mg), K$_2$CO$_3$ (81 mg), and potassium iodide (38 mg) in N-methyl-2-pyrrolidone (3 mL) is stirred at 100° C. for two days. After cooling to room temperature, ethyl acetate and water are added to the mixture. The organic phase is separated, dried over MgSO$_4$ and concentrated in vacuo. The residue is chromatographed on silica gel [dichloromethane/7 M ammonia in methanol 9:1→7:3] and the crude product is purified by preparative HPLC to give the title compound. LC (method 3): $t_R$=1.22 min; Mass spectrum (ESI$^+$): m/z=434 [M+H]$^+$.

Example 4

N-Cyclopropyl-3-fluoro-N[1-(2-fluoro-2-methyl-propyl)-piperidin-4-yl]-4-oxazol-5-yl-benzamide

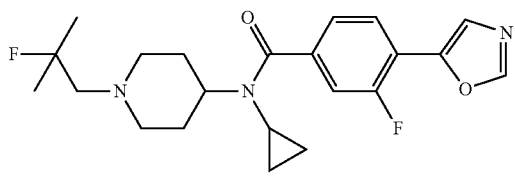 [SMILES: CC(C)(F)CN1CCC(N(C(=O)c2ccc(-c3cnco3)c(F)c2)C2CC2)CC1]

The title compound is prepared from N-cyclopropyl-3-fluoro-N-[1-(2-hydroxy-2-methyl-propyl)-piperidin-4-yl]-4-oxazol-5-yl-benzamide following a procedure analogous to that described for Example 1. LC (method 1): $t_R$=0.84 min; Mass spectrum (ESI$^+$): m/z=404 [M+H]$^+$.

Example 5

5-(4-Cyano-phenyl)-isoxazole-3-carboxylic acid cyclopropyl-[1-(1-trifluoromethyl-cyclopropylmethyl) -piperidin-4-yl]-amide

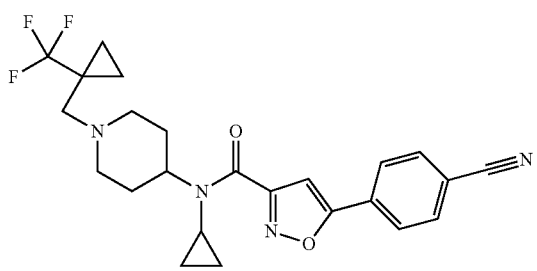 [SMILES: N#Cc1ccc(-c2cc(C(=O)N(C3CC3)C3CCN(CC4(C(F)(F)F)CC4)CC3)no2)cc1]

The title compound is prepared from 5-(4-cyano-phenyl)-isoxazole-3-carboxylic acid cyclopropyl-piperidin-4-yl-

Example 6

5-(4-Cyano-phenyl)-isoxazole-3-carboxylic acid cyclopropyl-[1-(2-fluoro-2-methyl-propyl)-piperidin-4-yl]-amide

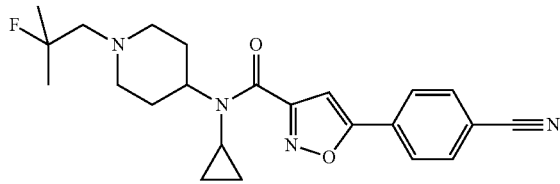 [SMILES: CC(C)(F)CN1CCC(N(C(=O)c2cc(-c3ccc(C#N)cc3)on2)C2CC2)CC1]

The title compound is prepared from 5-(4-cyano-phenyl)-isoxazole-3-carboxylic acid cyclopropyl-[1-(2-hydroxy-2-methyl-propyl)-piperidin-4-yl]-amide following a procedure analogous to that described for Example 1. LC (method 4): $t_R$=1.27 min; Mass spectrum (ESI+): m/z=411 [M+H]$^+$.

Example 7

3-(4-Cyano-2-fluoro-phenyl)-isoxazole-5-carboxylic acid cyclopropyl-[1-(1-trifluoromethyl-cyclopropyl-methyl)-piperidin-4-yl]-amide

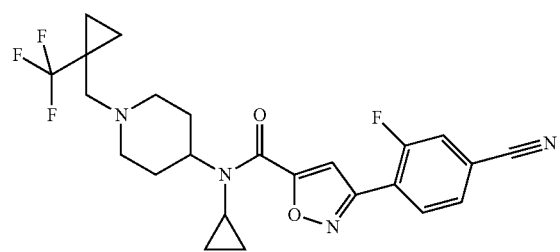 [SMILES: N#Cc1ccc(-c2cc(C(=O)N(C3CC3)C3CCN(CC4(C(F)(F)F)CC4)CC3)on2)c(F)c1]

The title compound is prepared from 3-(4-cyano-2-fluoro-phenyl)-isoxazole-5-carboxylic acid cyclopropyl-piperidin-4-yl-amide and methanesulfonic acid (1-trifluoromethyl-cyclopropyl)methyl ester following a procedure analogous to that described for Example 3. LC (method 4): $t_R$=1.35 min; Mass spectrum (ESI$^+$): m/z=477 [M+H]$^+$.

Example 8

3-(4-Cyano-2-fluoro-phenyl)-isoxazole-5-carboxylic acid cyclopropyl-[1-(2-fluoro-2-methyl-propyl)-piperidin-4-yl]-amide

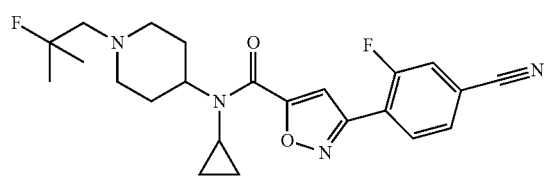 [SMILES: CC(C)(F)CN1CCC(N(C(=O)c2cc(-c3ccc(C#N)cc3F)no2)C2CC2)CC1]

The title compound is prepared from 3-(4-cyano-2-fluoro-phenyl)-isoxazole-5-carboxylic acid cyclopropyl-[1-(2-hydroxy-2-methyl-propyl)-piperidin-4-yl]-amide following a procedure analogous to that described for Example 1. LC (method 3): $t_R$=1.27 min; Mass spectrum (ESI$^+$): m/z=429 [M+H]$^+$.

Example 9

5-(4-Cyano-2-fluoro-phenyl)-isoxazole-3-carboxylic acid cyclopropyl-[1-(1-trifluoromethyl-cyclopropyl-methyl)-piperidin-4-yl]-amide

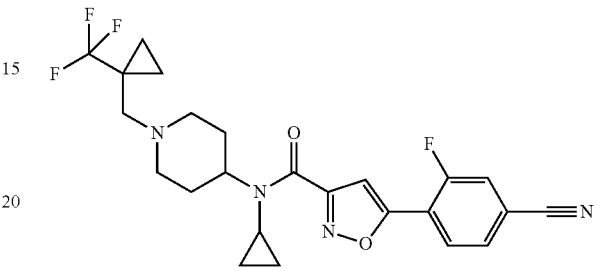

The title compound is prepared from 5-(4-cyano-2-fluoro-phenyl)-isoxazole-3-carboxylic acid cyclopropyl-piperidin-4-yl-amide and methanesulfonic acid (1-trifluoromethyl-cyclopropyl)methyl ester following a procedure analogous to that described for Example 3. LC (method 3): $t_R$=1.35 min; Mass spectrum (ESI$^+$): m/z=477 [M+H]$^+$.

Example 10

5-(4-Cyano-2-fluoro-phenyl)-isoxazole-3-carboxylic acid cyclopropyl-[1-(2-fluoro-2-methyl-propyl)-piperidin-4-yl]-amide

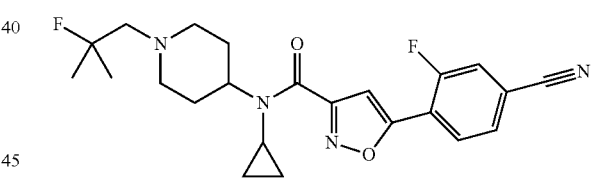

The title compound is prepared from 5-(4-cyano-2-fluoro-phenyl)-isoxazole-3-carboxylic acid cyclopropyl-[1-(2-hydroxy-2-methyl-propyl)-piperidin-4-yl]-amide following a procedure analogous to that described for Example 1. LC (method 5): $t_R$=0.81 min; Mass spectrum (ESI$^+$): m/z=429 [M+H]$^+$.

Examples 11-15

General procedure for the synthesis of the amides in table 1 from (3S,4R)-N-cyclopropyl-3-fluoro-1-{[1-(trifluoromethyl)cyclopropyl]methyl}piperidin-4-amine and their respective carboxylic acids Amines (~5 mg) and acids (~6-10 mg) are combined with triethylamine (0.015 mL) and 1-hydroxybenzotriazole (3 mg) in N,N-dimethylformamide (0.2 mL) and 1-ethyl-3-(3-dimethylaminopropyl)-carbodiimide (20 mg) is added in N,N-dimethylformamide (0.2 mL) and stirred at room temperature for 18 h. The product amides are purified by prep HPLC.

| Example | Structure | LC (method 8): $t_R$ [min] | Mass spectrum (APCI): m/z |
|---|---|---|---|
| 11 | 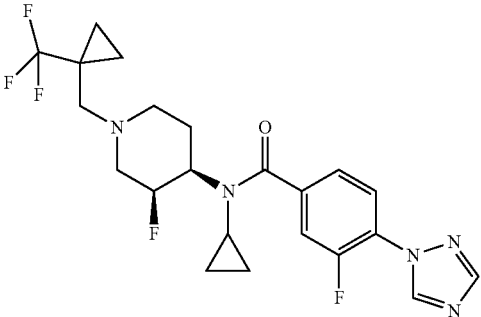<br>N-Cyclopropyl-3-fluoro-N-[(3S,4R)-3-fluoro-1-{[1-(trifluoromethyl)cyclopropyl]methyl}piperidin-4-yl]-4-(1H-1,2,4-triazol-1-yl)benzamide | 2.01 | 470.2 |
| 12 | 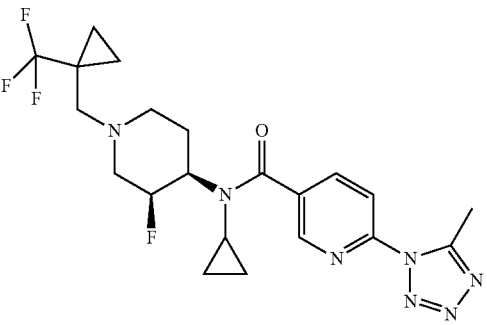<br>N-Cyclopropyl-N-[(3S,4R)-3-fluoro-1-{[1-(trifluoromethyl)cyclopropyl]methyl}piperidin-4-yl]-6-(5-methyl-1H-1,2,3,4-tetrazol-1-yl)pyridine-3-carboxamide | 2.02 | 468.2 |
| 13 | 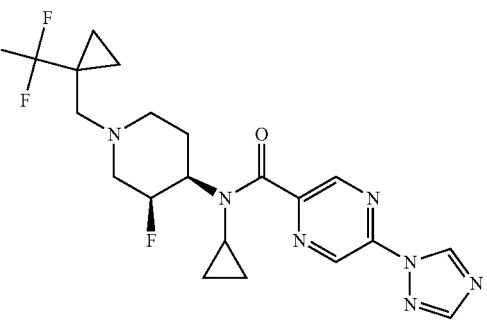<br>N-Cyclopropyl-N-[(3S,4R)-3-fluoro-1-{[1-(trifluoromethyl)cyclopropyl]methyl}piperidin-4-yl]-5-(1H-1,2,4-triazol-1-yl)pyrazine-2-carboxamide | 1.84 | 454.2 |

-continued

| Example | Structure | LC (method 8): $t_R$ [min] | Mass spectrum (APCI): m/z |
|---|---|---|---|
| 14 | N-Cyclopropyl-N-[(3S,4R)-3-fluoro-1-{[1-(trifluoromethyl)cyclopropyl]methyl}piperidin-4-yl]-2-(2-methyl-1H-imidazol-1-yl)pyrimidine-5-carboxamide | 1.46 | 467.2 |
| 15 | N-Cyclopropyl-N-[(3S,4R)-3-fluoro-1-{[1-(trifluoromethyl)cyclopropyl]methyl}piperidin-4-yl]-5-(3-methyl-1H-1,2,4-triazol-1-yl)pyrazine-2-carboxamide | 1.95 | 468.2 |

The invention claimed is:

1. A compound of formula I

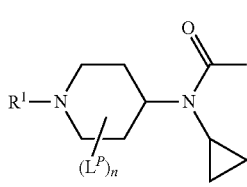

wherein:

$R^1$ is selected from a group consisting of —CH$_2$—$R^a$, wherein $R^a$ is C$_{1-6}$-alkyl optionally mono- or polysubstituted with fluorine, or C$_{3-6}$-cycloalkyl optionally mono- or polysubstituted with fluorine and optionally substituted with a group selected from CH$_3$, CF$_3$, and CHF$_2$;

(Het)Ar$^1$ is selected from a group consisting of phenyl and a 5- or 6-membered heteroaromatic ring which contains 1, 2, or 3 heteroatoms independently selected from N, NR$^N$, O, and S, wherein each phenyl and heteroaromatic ring is optionally substituted with one or more substituents selected from L$^Q$;

(Het)Ar$^2$ is

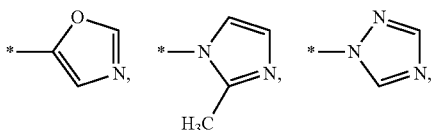

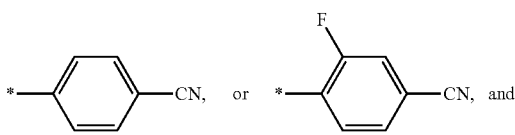

wherein $L^P$ is selected from a group consisting of F and $C_{1-3}$-alkyl, wherein the alkyl group is optionally substituted with one or more F-atoms;

T is selected from a group consisting of F, Cl, Br, I, CN, OH, NO$_2$, $C_{1-6}$-alkyl, $C_{2-6}$-alkenyl, $C_{2-6}$-alkynyl, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C(=O)—, $C_{1-4}$-alkyl-S(=O)—, $C_{1-4}$-alkyl-S(=O)$_2$—, $R^{NT1}R^{NT2}N$—, $R^{NT1}R^{NT2}N$—C(=O)—, $R^{NT1}R^{NT2}N$—S(=O)$_2$—, $R^{NT1}R^{NT2}N$—C(=O)—($R^N$)N—, heterocyclyl, heterocyclyl-O—, aryl, aryl-O—, heteroaryl, and heteroaryl-O—, wherein each alkyl, alkenyl, alkynyl, and cycloalkyl group is optionally substituted with one or more substituents independently selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C(=O)—, $C_{1-4}$-alkyl-S(=O)—, $C_{1-4}$-alkyl-S(=O)$_2$—, $R^{NT1}R^{NT2}N$—S(=O)$_2$—, aryl, heteroaryl, and heterocyclyl, and wherein heteroaryl is a 5- or 6-membered aromatic ring which contains 1, 2, 3, or 4 heteroatoms independently selected from N, NR$^N$, O, and S, and wherein heterocyclyl is a 4- to 7-membered unsaturated or saturated carbocyclic ring in which 1, 2, or 3-CH$_2$-groups are replaced independently by NR$^N$, O, —C(=O)—, S, —S(=O)—, or —S(=O)$_2$—, and/or in which a —CH-group is replaced by N, and wherein each aryl, heteroaryl, or heterocyclyl group is optionally substituted with one or more substituents independently selected from $L^{Ar}$;

$R^{NT1}$ is selected from a group consisting of H, $C_{1-6}$-alkyl, $C_{3-6}$-cycloalkyl, $C_{1-6}$-alkyl-C(=O)—, $C_{1-6}$-alkyl-S(=O)$_2$—, heterocyclyl, aryl, and heteroaryl, wherein each alkyl and cylcoalkyl group is optionally substituted with one or more substituents independently selected from the group consisting of F, OH, CN, $C_{1-4}$-alkyl-O—, $C_{1-4}$-alkyl-O—, $(R^N)_2$N, $C_{1-4}$-alkyl-S(=O)$_2$—, $C_{3-6}$-cycloalkyl, heterocyclyl, phenyl, and heteroaryl, and wherein heterocyclyl is a $C_{4-7}$-cycloalkyl ring in which 1 or 2-CH$_2$-groups independently are replaced by NR$^N$, O, C(=O), S, S(=O), or S(=O)$_2$, and wherein heterocyclyl is optionally substituted with one or more substituents independently selected from F, $C_{1-4}$-alkyl, $(R^N)_2$N, OH, and $C_{1-4}$-alkyl-O—, and wherein heteroaryl is a 5- or 6-membered aromatic ring which contains 1, 2, or 3 heteroatoms independently selected from N, NR$^N$, O, and S, and wherein each aryl, phenyl, and heteroaryl is optionally substituted with one or more substituents $L^{Ar}$;

$R^{NT2}$ is selected from a group consisting of H and $C_{1-6}$-alkyl; or $R^{NT1}$ and $R^{NT2}$ are linked to form a $C_{3-5}$-alkylene group, wherein 1 or 2—CH$_2$-groups are replaced independently by NR$^N$, O, C(=O), S, S(=O), or S(=O)$_2$, and wherein the ring formed by $R^{NT1}$ and $R^{NT2}$ together with the nitrogen atom to which they are attached is optionally substituted with one or more substituents independently selected from F, $C_{1-4}$-alkyl, $(R^N)_2$N—, OH, and $C_{1-4}$-alkyl-O—;

$L^{Ar}$ is selected from a group consisting of F, Cl, Br, I, CN, OH, NO$_2$, $C_{1-4}$-alkyl-O—, $(R^N)_2$N—C(=O)—, $(R^N)_2$N—, and $C_{1-4}$-alkyl-S(=O)$_2$—, wherein each alkyl group is optionally substituted with one or more substituents independently selected from F, Cl, CN, OH, and $C_{1-3}$-alkyl-O—;

$L^Q$ is selected from a group consisting of F, Cl, CN, OH, $C_{1-4}$-alkyl, $C_{3-7}$-cycloalkyl, F$_2$HC—, F$_3$C—, $C_{1-4}$-alkyl-O—, F$_2$HC—O—, F$_3$C—O—, and $C_{3-7}$-cycloalkyl-O—;

n is an integer selected from 0, 1, 2, 3, or 4;

$R^N$ is independently selected from a group consisting of H, $C_{1-4}$-alkyl, $C_{1-4}$-alkyl-C(=O)—, and $C_{1-4}$-alkyl-S(=O)$_2$—; and aryl is phenyl or naphthyl, or a tautomer or stereoisomer thereof, or a salt thereof.

2. The compound according to claim 1, wherein $R^1$ is

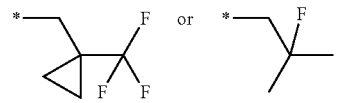

3. The compound according to claim 1, wherein: (Het)Ar$^1$ is

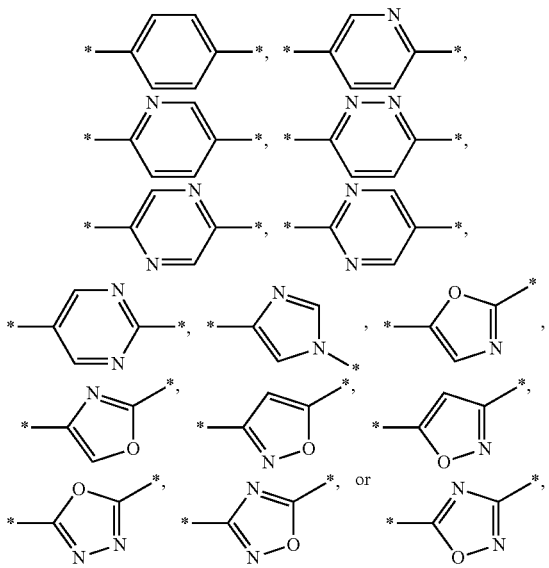

wherein the group (Het)Ar$^2$ is attached to the right-hand side and the carbonyl group in formula I is attached to the left-hand side of each of these groups, and wherein the phenylene group is optionally additionally substituted with one F atom.

4. The compound according to claim 1, wherein: (Het)Ar$^1$ is

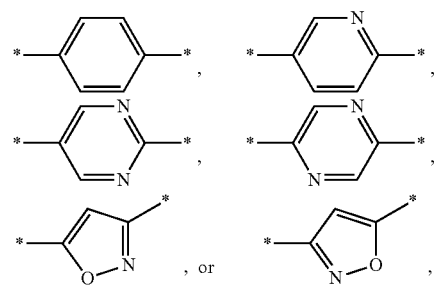

wherein the group (Het)Ar$^2$ is attached to the right-hand side and the carbonyl group in formula I is attached to the left-hand side of each of these groups, and wherein the phenylene group is optionally additionally substituted with one F atom.

5. The compound according to claim 1, wherein n is 0 or 1 and $L^P$ is F.

6. The compound of formula I according to claim 1, wherein:

$R^1$ is

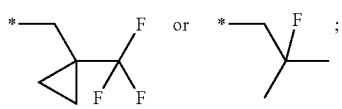

(Het)Ar$^1$-(Het)Ar$^2$ is

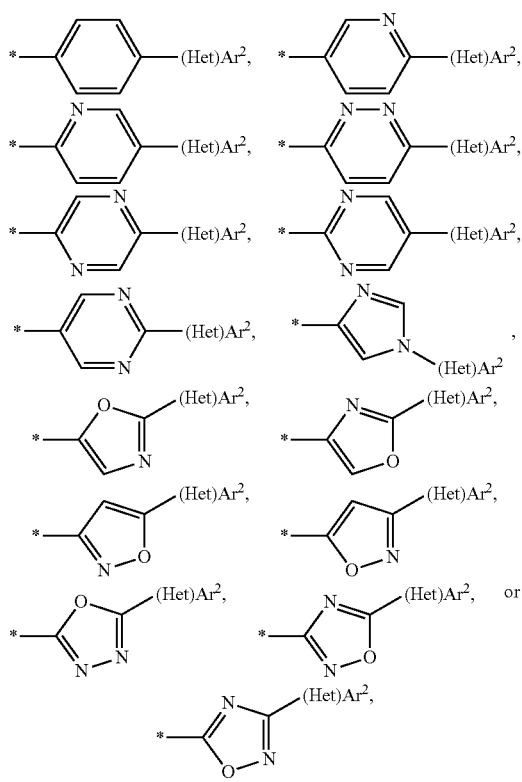

wherein the phenylene group is optionally additionally substituted with one F atom, and $L^P$ is F and n is 0 or 1.

7. The compound of formula I according to claim 1, wherein:

$R^1$ is

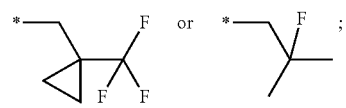

(Het)Ar$^1$-(Het)Ar$^2$ is

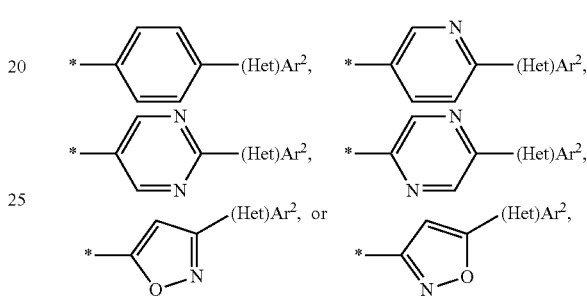

wherein the phenylene group is optionally additionally substituted with one F; and $L^P$ is F and n is 0 or 1.

8. The pharmaceutically acceptable salt of a compound according to claim 1.

9. A pharmaceutical composition comprising one or more compounds according to claim 1 or a pharmaceutically acceptable salts thereof, and an inert carriers or diluents.

10. A method for treating diabetes, dislipidemia, or obesity, comprising administering to a patient in need thereof the compound according to claim 1 or a pharmaceutically acceptable salt thereof.

11. A pharmaceutical composition comprising a compound according claim 1 or a pharmaceutically acceptable salt thereof, an additional therapeutic agents, and an inert carriers or diluents.

* * * * *